(12) United States Patent
Mallery et al.

(10) Patent No.: US 11,484,591 B2
(45) Date of Patent: Nov. 1, 2022

(54) CHEMOPREVENTION USING CONTROLLED-RELEASE FORMULATIONS OF ANTI-INTERLEUKIN 6 AGENTS, SYNTHETIC VITAMIN A ANALOGUES OR METABOLITES, AND ESTRADIOL METABOLITES

(71) Applicants: OHIO STATE INNOVATION FOUNDATION, Columbus, OH (US); THE REGENTS OF THE UNIVERSITY OF MICHIGAN, Ann Arbor, MI (US)

(72) Inventors: Susan Regina Mallery, Columbus, OH (US); Steven Paul Schwendeman, Superior Township, MI (US)

(73) Assignees: OHIO STATE INNOVATION FOUNDATION, Columbus, OH (US); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/078,860

(22) PCT Filed: Feb. 22, 2017

(86) PCT No.: PCT/US2017/018912
§ 371 (c)(1),
(2) Date: Aug. 22, 2018

(87) PCT Pub. No.: WO2017/147169
PCT Pub. Date: Aug. 31, 2017

(65) Prior Publication Data
US 2019/0091330 A1    Mar. 28, 2019

Related U.S. Application Data

(60) Provisional application No. 62/298,244, filed on Feb. 22, 2016.

(51) Int. Cl.
| | | |
|---|---|---|
| A61K 39/395 | (2006.01) | |
| A61K 31/565 | (2006.01) | |
| A61K 31/167 | (2006.01) | |
| A61K 45/00 | (2006.01) | |
| A61K 47/10 | (2017.01) | |
| A61K 31/74 | (2006.01) | |
| C07K 16/28 | (2006.01) | |
| A61P 35/00 | (2006.01) | |
| A61K 39/00 | (2006.01) | |

(52) U.S. Cl.
CPC ........ *A61K 39/3955* (2013.01); *A61K 31/167* (2013.01); *A61K 31/565* (2013.01); *A61K 31/74* (2013.01); *A61K 45/00* (2013.01); *A61K 47/10* (2013.01); *A61P 35/00* (2018.01); *C07K 16/2866* (2013.01); *A61K 2039/505* (2013.01); *C07K 2317/24* (2013.01)

(58) Field of Classification Search
None
See application file for complete search history.

(56) References Cited

U.S. PATENT DOCUMENTS

| | | |
|---|---|---|
| 5,171,840 A | 12/1992 | Kishimoto |
| 5,480,796 A | 1/1996 | Kishimoto |
| 5,578,325 A | 11/1996 | Domb et al. |
| 5,670,373 A | 9/1997 | Kishimoto |
| 5,795,965 A | 8/1998 | Tsuchiya et al. |
| 5,817,790 A | 10/1998 | Tsuchiya et al. |
| 5,851,793 A | 12/1998 | Kishimoto |
| 5,888,510 A | 3/1999 | Kishimoto et al. |
| 5,990,282 A | 11/1999 | Kishimoto |
| 6,007,845 A | 12/1999 | Domb et al. |
| 6,086,874 A | 7/2000 | Yoshida et al. |
| 6,261,560 B1 | 7/2001 | Tsujinaka et al. |
| 6,410,691 B1 | 6/2002 | Kishimoto |
| 6,428,979 B1 | 8/2002 | Kishimoto |
| 6,537,782 B1 | 3/2003 | Shibuya et al. |
| 6,692,742 B1 | 2/2004 | Nakamura et al. |
| 6,723,319 B1 | 4/2004 | Ito et al. |

(Continued)

FOREIGN PATENT DOCUMENTS

| | | |
|---|---|---|
| WO | 00/10607 | 3/2000 |
| WO | 2011/013786 | 2/2011 |

OTHER PUBLICATIONS

Arora, Amit, and Eric M. Scholar. "Role of tyrosine kinase inhibitors in cancer therapy." Journal of Pharmacology and Experimental Therapeutics 315.3 (2005): 971-979.

(Continued)

*Primary Examiner* — Marianne P Allen
(74) *Attorney, Agent, or Firm* — Marshall, Gerstein & Borun LLP

(57) ABSTRACT

The present disclosure is directed to formulations and methods for treatment of disease such as chemoprevention of cancer, for example oral squamous cell carcinoma (OSCC), and for methods of preparing the formulations. Further, the disclosure relates to local administration in slow release dosage forms for treatment of disease. The extended-release formulations are comprised of biodegradable polymeric implants (for example millicylinders and microspheres as well as in situ forming gels) and therapeutic agents selected from an anti-interleukin 6 agent, a synthetic vitamin A analogue and/or metabolite, and/or an estradiol metabolite for the local delivery of therapeutic agents to a site where a cancer has been previously excised or to prevent progression of a precancerous lesion.

3 Claims, 20 Drawing Sheets

(56) References Cited

U.S. PATENT DOCUMENTS

| | | | |
|---|---|---|---|
| 6,962,812 B2 | 11/2005 | Shibuya et al. | |
| 7,320,792 B2 | 1/2008 | Ito et al. | |
| 7,332,289 B2 | 2/2008 | Takeda et al. | |
| 7,479,543 B2 | 1/2009 | Tsuchiya et al. | |
| 7,521,052 B2 | 4/2009 | Okuda et al. | |
| 7,566,453 B2 | 7/2009 | Nakamura et al. | |
| 7,771,723 B2 | 8/2010 | Nakamura et al. | |
| 7,824,674 B2 | 11/2010 | Ito et al. | |
| 7,927,815 B2 | 4/2011 | Takeda et al. | |
| 7,955,598 B2 | 6/2011 | Yoshizaki et al. | |
| 8,231,892 B2 * | 7/2012 | Lyons | A61P 29/00 424/428 |
| 8,440,196 B1 | 5/2013 | Funakoshi et al. | |
| 2001/0001663 A1 | 5/2001 | Kishimoto et al. | |
| 2002/0131967 A1 | 9/2002 | Nakamura et al. | |
| 2002/0187150 A1 | 12/2002 | Mihara et al. | |
| 2003/0096372 A1 | 5/2003 | Shibuya et al. | |
| 2003/0190316 A1 | 10/2003 | Kakuta et al. | |
| 2004/0028681 A1 | 2/2004 | Ito et al. | |
| 2004/0071706 A1 | 4/2004 | Ito et al. | |
| 2004/0115197 A1 | 6/2004 | Yoshizaki et al. | |
| 2004/0138424 A1 | 7/2004 | Takeda et al. | |
| 2004/0247621 A1 | 12/2004 | Nakamura et al. | |
| 2005/0118163 A1 | 6/2005 | Mizushima et al. | |
| 2005/0142635 A1 | 6/2005 | Tsuchiya et al. | |
| 2005/0214278 A1 | 9/2005 | Kakuta et al. | |
| 2005/0238644 A1 | 10/2005 | Mihara et al. | |
| 2006/0134113 A1 | 6/2006 | Mihara | |
| 2006/0142549 A1 | 6/2006 | Takeda et al. | |
| 2006/0165696 A1 | 7/2006 | Okano et al. | |
| 2006/0251653 A1 | 11/2006 | Okuda et al. | |
| 2006/0292147 A1 | 12/2006 | Yoshizaki et al. | |
| 2007/0036785 A1 | 2/2007 | Kishimoto et al. | |
| 2007/0098714 A1 | 5/2007 | Nishimoto et al. | |
| 2007/0134242 A1 | 6/2007 | Nishimoto et al. | |
| 2007/0148169 A1 | 6/2007 | Yoshizaki et al. | |
| 2007/0243189 A1 | 10/2007 | Yoshizaki et al. | |
| 2008/0124325 A1 | 5/2008 | Ito et al. | |
| 2008/0124761 A1 | 5/2008 | Goto et al. | |
| 2008/0255342 A1 | 10/2008 | Takeda et al. | |
| 2008/0274106 A1 | 11/2008 | Nishimoto et al. | |
| 2008/0306247 A1 | 12/2008 | Mizushima et al. | |
| 2009/0022719 A1 | 1/2009 | Mihara et al. | |
| 2009/0131639 A1 | 5/2009 | Kakuta et al. | |
| 2009/0181029 A1 | 7/2009 | Okuda et al. | |
| 2009/0220499 A1 | 9/2009 | Yasunami | |
| 2009/0220500 A1 | 9/2009 | Kobara | |
| 2009/0263384 A1 | 10/2009 | Okada et al. | |
| 2009/0269335 A1 | 10/2009 | Nakashima et al. | |
| 2009/0291076 A1 | 11/2009 | Morichika et al. | |
| 2010/0008907 A1 | 1/2010 | Nishimoto et al. | |
| 2010/0034811 A1 | 2/2010 | Ishida | |
| 2010/0061986 A1 | 3/2010 | Takahashi et al. | |
| 2010/0129355 A1 | 5/2010 | Ohguro et al. | |
| 2010/0247523 A1 | 9/2010 | Kano et al. | |
| 2010/0255007 A1 | 10/2010 | Mihara et al. | |
| 2010/0285011 A1 | 11/2010 | Morichika et al. | |
| 2010/0304400 A1 | 12/2010 | Stubenrauch et al. | |
| 2011/0117087 A1 | 5/2011 | Franze et al. | |
| 2011/0150869 A1 | 6/2011 | Mitsunaga et al. | |
| 2012/0183539 A1 | 7/2012 | Maeda | |
| 2013/0202659 A1 * | 8/2013 | Crawford | A61K 47/60 424/400 |
| 2014/0056949 A1 | 2/2014 | Mallery et al. | |
| 2015/0037320 A1 | 2/2015 | Mcgrath et al. | |
| 2015/0164805 A1 | 6/2015 | Schwendeman et al. | |
| 2015/0342894 A1 * | 12/2015 | Anderson | A61K 9/0092 424/490 |

OTHER PUBLICATIONS

Bahleda, Rastislav, et al. "Phase I study of afatinib combined with nintedanib in patients with advanced solid tumours." British journal of cancer 113.10 (2015): 1413.

Berman, Helen, Kim Henrick, and Haruki Nakamura. "Announcing the worldwide protein data bank." Nature Structural and Molecular Biology 10.12 (2003): 980.

Brockstein, Bruce E. "Management of Recurrent Head and Neck Cancer." Drugs 71.12 (2011): 1551-1559.

Brooks, Heather D., et al. "Phase 2 study of dasatinib in the treatment of head and neck squamous cell carcinoma." Cancer 117.10 (2011): 2112-2119.

Brown, J. Martin, and Laura D. Attardi. "The role of apoptosis in cancer development and treatment response." Nature reviews cancer 5.3 (2005): 231.

Campos-Sandoval, Jose Angel, et al. "Fenretinide derivatives act as disrupters of interactions of serum retinol binding protein (sRBP) with transthyretin and the sRBP receptor." Journal of medicinal chemistry 54.13 (2011): 4378-4387.

Chalaris, Athena, et al. "The soluble Interleukin 6 receptor: generation and role in inflammation and cancer." European journal of cell biology 90.6-7 (2011): 484-494.

Chang, Pi-Yueh, et al. "Association and prognostic value of serum inflammation markers in patients with leukoplakia and oral cavity cancer." Clinical chemistry and laboratory medicine 51.6 (2013): 1291-1300.

Desai, Kashappa Goud H., Susan R. Mallery, and Steven P. Schwendeman. "Effect of formulation parameters on 2-methoxyestradiol release from injectable cylindrical poly (DL-lactide-co-glycolide) implants." European Journal of Pharmaceutics and Biopharmaceutics 70.1 (2008): 187-198.

Dziadziuszko, R., and J. Jassem. "Epidermal growth factor receptor (EGFR) inhibitors and derived treatments." annals of Oncology 23.suppl_10 (2012): x193-x196.

Fofaria, Neel M., and Sanjay K. Srivastava. "STAT3 induces anoikis resistance, promotes cell invasion and metastatic potential in pancreatic cancer cells." Carcinogenesis 36.1 (2014): 142-150.

Furtek, Steffanie L., et al. "Strategies and approaches of targeting STAT3 for cancer treatment." ACS chemical biology 11.2 (2016): 308-318.

Fury, Matthew G., et al. "Phase II study of saracatinib (AZD0530) for patients with recurrent or metastatic head and neck squamous cell carcinoma (HNSCC)." Anticancer research 31.1 (2011): 249-253.

Garcia, Roy, et al. "Constitutive activation of Stat3 by the Src and JAK tyrosine kinases participates in growth regulation of human breast carcinoma cells." Oncogene 20.20 (2001): 2499.

Gleber-Netto, Frederico O., et al. "Molecular events in relapsed oral squamous cell carcinoma: Recurrence vs secondary primary tumor." Oral oncology 51.8 (2015): 738-744.

Han BB, Li S, Tong M, Holpuch AS, Spinney R, Wang D, et al. Fenretinide perturbs focal adhesion kinase in premalignant and malignant human Oral Keratinocytes. Fenretinide's chemopreventive mechanisms include ECM interactions. Cancer Prev Res 2015;8:419-30.

Hantschel, Oliver, and Giulio Superti-Furga. "Regulation of the c-Abl and Bcr-Abl tyrosine kinases." Nature reviews Molecular cell biology 5.1 (2004): 33.

Harada, Koji, et al. "Cepharanthine inhibits angiogenesis and tumorigenicity of human oral squamous cell carcinoma cells by suppressing expression of vascular endothelial growth factor and interleukin-8." International journal of oncology 35.5 (2009): 1025-1035.

Huber, Michaell A., and Bundhit Tantiwongkosi. "Oral and oropharyngeal cancer." Medical Clinics 98.6 (2014): 1299-1321.

Jemaa, Awatef Ben, et al. "The proinflammatory cytokine, IL-6, and its interference with bFGF signaling and PSMA in prostate cancer cells." Inflammation 36.3 (2013): 643-650.

Jinno, Teppei, et al. "Increased expression of interleukin-6 predicts poor response to chemoradiotherapy and unfavorable prognosis in oral squamous cell carcinoma." Oncology reports 33.5 (2015): 2161-2168.

Jones, Simon A., Jürgen Scheller, and Stefan Rose-John. "Therapeutic strategies for the clinical blockade of IL-6/gp130 signaling." The Journal of clinical investigation 121.9 (2011): 3375-3383.

(56) References Cited

OTHER PUBLICATIONS

Kumar, Addanki P., et al. "2-Methoxyestradiol interferes with NFκB transcriptional activity in primitive neuroectodermal brain tumors: implications for management." Carcinogenesis 24.2 (2003): 209-216.
Lee, Che-Hsin, et al. "Tumorsphere as an effective in vitro platform for screening anti-cancer stem cell drugs." Oncotarget 7.2 (2016): 1215.
Lee, Heehyoung, et al. "Acetylated STAT3 is crucial for methylation of tumor-suppressor gene promoters and inhibition by resveratrol results in demethylation." Proceedings of the National Academy of Sciences 109.20 (2012): 7765-7769.
Lee, Tin Lap, et al. "Epigenetic modification of SOCS-1 differentially regulates STAT3 activation in response to interleukin-6 receptor and epidermal growth factor receptor signaling through JAK and/or MEK in head and neck squamous cell carcinomas." Molecular cancer therapeutics 5.1 (2006): 8-19.
Lin, J., and R. Arlinghaus. "Activated c-Abl tyrosine kinase in malignant solid tumors." Oncogene 27.32 (2008): 4385.
Logue, Jeremy S., and Deborah K. Morrison. "Complexity in the signaling network: insights from the use of targeted inhibitors in cancer therapy." Genes & development 26.7 (2012): 641-650.
Mathiowitz, E., M. D. Cohen, and R. Langer. "Novel microcapsules for delivery systems." Reactive Polymers, Ion Exchangers, Sorbents 6.2-3 (1987): 275-283.
Mathiowitz, E., and R. Langer. "Polyanhydride microspheres as drug carriers I. Hot-melt microencapsulation." Journal of controlled release 5.1 (1987): 13-22.
Mathiowitz, Edith, et al. "Polyanhydride microspheres as drug carriers. II. Microencapsulation by solvent removal." Journal of Applied Polymer Science 35.3 (1988): 755-774.
Molife, L. Rhoda, et al. "Randomized Phase II trial of nintedanib, afatinib and sequential combination in castration-resistant prostate cancer." Future oncology 10.2 (2014): 219-231.
Mooberry, Susan L. "Mechanism of action of 2-methoxyestradiol: new developments." Drug Resistance Updates 6.6 (2003): 355-361.
Mueck, A. O., and H. Seeger. "2-Methoxyestradiol—biology and mechanism of action." Steroids 75.10 (2010): 625-631.
Murray, Christopher B., A. CR Kagan, and M. G. Bawendi. "Synthesis and characterization of monodisperse nanocrystals and close-packed nanocrystal assemblies." Annual Review of Materials Science 30.1 (2000): 545-610.
Naithani, Rajesh, et al. "Comprehensive review of cancer chemopreventive agents evaluated in experimental carcinogenesis models and clinical trials." Current medicinal chemistry 15.11 (2008): 1044-1071.
Ogura, Michinori, et al. "Phase I study of OPB-51602, an oral inhibitor of signal transducer and activator of transcription 3, in patients with relapsed/refractory hematological malignancies." Cancer science 106.7 (2015): 896-901.
Paolicelli, Patrizia, et al. "Surface-modified PLGA-based nanoparticles that can efficiently associate and deliver virus-like particles." Nanomedicine 5.6 (2010): 843-853.
Pellegrino, Teresa, et al. "On the development of colloidal nanoparticles towards multifunctional structures and their possible use for biological applications." small 1.1 (2005): 48-63.
Poindessous, Virginie, et al. "EGFR-and VEGF (R)-targeted small molecules show synergistic activity in colorectal cancer models refractory to combinations of monoclonal antibodies." Clinical Cancer Research (2011) 17:6522-30.
Ricker, Justin L., et al. "2-Methoxyestradiol inhibits hypoxia-inducible factor 1α, tumor growth, and angiogenesis and augments paclitaxel efficacy in head and neck squamous cell carcinoma." Clinical Cancer Research 10.24 (2004): 8665-8673.
Shinriki, Satoru, et al. "Humanized anti-interleukin-6 receptor antibody suppresses tumor angiogenesis and in vivo growth of human oral squamous cell carcinoma." Clinical Cancer Research (2009) 15:5426-34.
Specenier, Pol, and Jan B. Vermorken. "Cetuximab: its unique place in head and neck cancer treatment." Biologics: targets & therapy 7 (2013): 77.
Stanam, Aditya, et al. "Upregulated interleukin-6 expression contributes to erlotinib resistance in head and neck squamous cell carcinoma." Molecular oncology 9.7 (2015): 1371-1383.
Suh, Young-Ah, et al. "Inhibition of IL-6/STAT3 axis and targeting Axl and Tyro3 receptor tyrosine kinases by apigenin circumvent taxol resistance in ovarian cancer cells." International journal of oncology 46.3 (2015): 1405-1411.
Sun, Chong, and René Bernards. "Feedback and redundancy in receptor tyrosine kinase signaling: relevance to cancer therapies." Trends in biochemical sciences 39.10 (2014): 465-474.
Takahashi, Noriko, Edward A. Sausville, and Theodore R. Breitman. "N-(4-hydroxyphenyl) retinamide (Fenretinide) in combination with retinoic acid enhances differentiation and retinoylation of proteins." Clinical cancer research 1.6 (1995): 637-642.
Trindade, Tito, Paul O'Brien, and Nigel L. Pickett. "Nanocrystalline semiconductors: synthesis, properties, and perspectives." Chemistry of Materials 13.11 (2001): 3843-3858.
Trott, Oleg, and Arthur J. Olson. "AutoDock Vina: improving the speed and accuracy of docking with a new scoring function, efficient optimization, and multithreading." Journal of computational chemistry 31.2 (2010): 455-461.
Walsh, John G., et al. "Caspase-1 promiscuity is counterbalanced by rapid inactivation of the processed enzyme." Journal of Biological Chemistry (2011);286:32513-24.
Ward, Kristy K., et al. "Inhibition of focal adhesion kinase (FAK) activity prevents anchorage-independent ovarian carcinoma cell growth and tumor progression." Clinical & experimental metastasis 30.5 (2013): 579-594.
Wong, A. L., et al. "Phase I and biomarker study of OPB-51602, a novel signal transducer and activator of transcription (STAT) 3 inhibitor, in patients with refractory solid malignancies." Annals of Oncology 26.5 (2015): 998-1005.
Yang, Jinbo, et al. "Unphosphorylated STAT3 accumulates in response to IL-6 and activates transcription by binding to NFκB." Genes & development 21.11 (2007): 21:1396-1408.
Yu, Hua, Drew Pardoll, and Richard Jove. "STATs in cancer inflammation and immunity: a leading role for STAT3." Nature Reviews Cancer 9.11 (2009): 798.
Yu, Hua, et al. "Revisiting STAT3 signalling in cancer: new and unexpected biological functions." Nature reviews Cancer 14.11 (2014): 736.
Yu, Wenying, et al. "Discovery of novel STAT3 small molecule inhibitors via in silico site-directed fragment-based drug design." Journal of medicinal chemistry 56.11 (2013): 4402-4412.
Yu Y, Wan Y, Huang C. "The biological functions of NF-κB1 (p50) and its potential as an anti-cancer target." Curr Cancer Drug Targets 2009: 9:566-71.
Zhang, Lisha, et al. "Nanoparticles in medicine: therapeutic applications and developments." Clinical pharmacology & therapeutics 83.5 (2008): 761-769.
Mallery, S. R., Wang, D., Santiago, B., Pei, P., Schwendeman, S., Nieto, K., . . . & Holpuch, A. S. (2016). Benefits of Multifaceted Chemopreventives in the Suppression of the Oral Squamous Cell Carcinoma (OSCC) Tumorigenic Phenotype. Cancer Prevention Research, canprevres-0180.
U.S. Patent and Trademark Office. International Search Report and Written Opinion of the International Searching Authority, dated May 3, 2017. 13 pages.
Zhou, T. et al.; "Development of a multiple-drug delivery Implant for Intraocularmanagement of proliferative vitreoretinopathy;" *Journal of Controlled Release* 55 (1998) 281-295.
Zhu, G. et al.; "Stabilization of proteins encapsulated in Injectable poly (lactlde-co-glycollde);" *Nature Biotechnology* vol. 18, Jan. 2000 (pp. 52-57).
Zhang, Y. et al.; "Design of Controlled Release PLGA Microspheres for Hydrophobic Fenretinide;" Mol. Pharmaceutics 2016, 13, (pp. 2622-2630).

(56) References Cited

OTHER PUBLICATIONS

Nieto, K. et al.; "In vivo controlled release of fenretinide from long-acting release depots for chemoprevention of oral squamous cell carcinoma recurrence;" *International Journal of Pharmaceutics* 538, 2018, (pp. 48-56).

Holpuch, A. et al.; "Optimizing Therapeutic Efficacy of Chemopreventive Agents: A Critical Review of Delivery Strategies in Oral Cancer Chemoprevention Clinical Trials;" *Journal of Carcinogenesis* 2011, 10:23 (pp. 1-11).

\* cited by examiner

|  | JSCC1 | JSCC2 | JSCC3 |
|---|---|---|---|
| Angiogenin | A7-8 | A7-8 |  |
| Dickkopf-1 | B15-16 | B15-16 | B15-16 |
| EMMPRIN |  | B21-22 |  |
| ENA-78 (CXCL5) |  | C3-4 |  |
| Fibroblast Growth Factor 19 |  | C13-14 |  |
| GRO-alpha (CXCL1) | D1-2 | D1-2 |  |
| Intercellular Adhesion Molecule-1 |  | D7-8 |  |
| Insulin-like Growth Factor Binding Protein-2 | D11-12 |  | D11-12 |
| Insulin-like Growth Factor Binding Protein-3 |  | D13-14 |  |
| Interleukin-1alpha |  | D15-16 |  |
| Interleukin-6 |  | E5-6 |  |
| Interleukin-8 | E7-8 | E7-8 | E7-8 |
| Interleukin-17A |  | E21-22 |  |
| Lipocalin-2 |  | G5-6 |  |
| Monocyte Chemotactic Protein-1 (CCL2) | G7-8 |  | G7-8 |
| Microphage Migration Inhibitory Factor | G13-14 | G13-14 | G13-14 |
| PDGF-AA | H5-6 | H5-6 |  |
| SerpinE1 | I1-2 | I1-2 | I1-2 |
| Transferrin Receptor |  | I11-12 |  |
| Thrombospondin-1 |  | I15-16 |  |
| Urokinase Receptor |  | I19-20 |  |

FIG. 1D

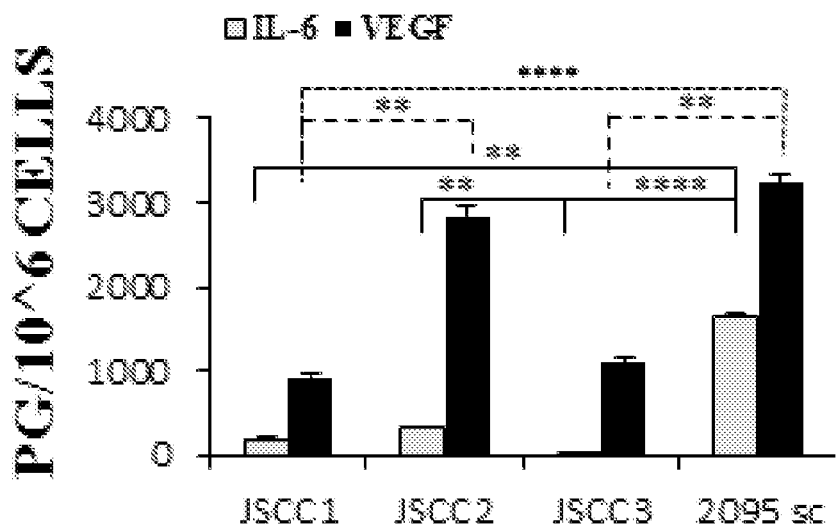

FIG. 1E

STAT3

| Compound | Binding energy (kcal/mol) | Kd | IC$_{50}$(nM) |
|---|---|---|---|
| 4-oxo-4HPR | -7.4 | 3.74E-06 | |
| 4-HPR | -8<br>-14.2*Novel binding site | 1.36E-06 | |
| Retinol | -6.8 | 1.03E-05 | |
| Cpd30 | -7.2 | 5.24E-06 | 30 |
| Cpd188 | -7 | 7.35E-06 | 20 |
| EpYINQ | -7.8 | 1.90E-06 | |
| LLL12 | -9 | 2.51E-07 | 0.16-3.09 |
| LYS5 | -8 | 1.36E-06 | 74 |
| Paper9 | -8.3 | 8.18E-07 | 0.033 |
| Paper-11-9b | -9.7 | 7.69E-08 | 0.38 |
| Niclosamide | -7.1 | 6.21E-06 | 0.25 |
| S31-201 | -7.7 | 5.83E-07 | 86 |
| S31-M2001 | -9 | 2.51E-07 | 42 |
| S31-M2001-H | -8.8 | 3.52E-07 | 42 |
| SF-1-066 | -8.6 | 4.93E-07 | 35 |
| STA-21 | -10.2 | 3.30E-08 | 20 |
| Stattic | -7 | 7.35E-06 | 5.1 |
| STX-0119 | -10.8 | 1.20E-08 | 74 |
| XZH-5 | -8.5 | 5.83E-07 | 25 |
| Pro-p Tyr-leu-lys-thr-lys (PpYLKTK) | -7.9 | 1.61E-06 | |

| Compound | Binding energy (kcal/mol) | Kd | IC$_{50}$(nM) |
|---|---|---|---|
| 4-oxo-4HPR | -9.9 | 5.49E-08 | |
| 4HPR | -10.6 | 1.68E-08 | |
| Retinol | -9.1 | 2.12E-07 | |
| ATP | -8.2 | 5.83E-07 | |
| ATP-Mg | -9.2 | 2.51E-07 | |
| Abz-EpYINQ | -9.5 | 1.08E-07 | 26 |
| AP23464 | -10.6 | 1.68E-08 | 22 |
| AZD0530 | -9.9 | 5.49E-08 | 2.7 |
| Bafetinib | -10.9 | 1.01E-08 | |
| Bosutinib | -9.7 | 7.69E-08 | 3.8 |
| Dastinib | -9.5 | 1.08E-07 | 0.55 |
| KX2-391 | -10.2 | 3.30E-08 | Sep-60 |
| AMN107 | -11.5 | 3.68E-09 | |
| PD173955 | -10.1 | 3.91E-08 | 22 |
| Ruxolitinb | -8.7 | 1.15E-06 | 2920 |
| STI-571 | -11.4 | 4.36E-09 | 100 |
| STI-571 v2 | -11.2 | 6.11E-09 | 1633 | c-Abl

| Compound | Binding energy (kcal/mol) | Kd | IC$_{50}$(nM) |
|---|---|---|---|
| 4-oxo-4HPR | -11.8 | 2.22E-09 | |
| 4HPR | -12.2 | 1.13E-09 | |
| Retinol | -10.9 | 1.01E-08 | |
| ATP | -8.6 | 1.90E-06 | |
| ATP-Mg | -9.5 | 1.28E-07 | |
| Abz-EpYINQ | -10.2 | 3.30E-08 | 1 |
| AP23464 | -12 | 1.58E-09 | |
| AZD0530 | -11 | 8.56E-09 | 30 |
| Bafetinib | -11.6 | 3.11E-09 | 5.8 |
| Bosutinib | -10.8 | 1.20E-08 | 1 |
| Dastinib | -9.7 | 7.69E-08 | 1 |
| KX2-391 | -10.6 | 1.68E-08 | |
| AMN107 | -12.8 | 4.10E-10 | 30 |
| PD173955 | -11.7 | 2.62E-09 | |
| Ruxolitinb | -10.3 | 2.79E-08 | |
| STI-571 | -12.1 | 1.34E-09 | |
| STI-571 v2 | -11.7 | 2.62E-09 | |

| TX Groups | Pre (mm³) | Post (mm³) | Fold-change |
|---|---|---|---|
| CTR | 159.8 ± 17.8 | 575.7 ± 63.3 | 3.60 |
| 2ME | 213.3 ± 20.4 | 809.8 ± 109.6 | 3.80 |
| 4HTR | 113.7 ± 18.9 | 578.4 ± 77.7 | 5.08 |
| TOC | 108.3 ± 19.2 | 230.1 ± 52.2 | 2.19 |
| 2ME+4HPR | 149.2 ± 19.8 | 515.1 ± 82.8 | 3.45 |
| 2ME+TOC | 276.3 ± 73.6 | 647.9 ± 102.5 | 2.34 |
| TOC+4HPR | 169.3 ± 24.6 | 315.5 ± 97.6 | 1.86 |
| 2ME+TOC+4HPR | 211.8 ± 30.9 | 364.4 ± 83.3 | 1.72 |

CHEMOPREVENTION USING CONTROLLED-RELEASE FORMULATIONS OF ANTI-INTERLEUKIN 6 AGENTS, SYNTHETIC VITAMIN A ANALOGUES OR METABOLITES, AND ESTRADIOL METABOLITES

CROSS-REFERENCE TO RELATED APPLICATIONS

This application is a national stage application filed under 35 U.S.C. § 371 of PCT/US2017/018912 filed Feb. 22, 2017, which claims the benefit of U.S. Provisional Patent Application Ser. No. 62/298,244 filed Feb. 22, 2016, the disclosure of which is expressly incorporated herein by reference.

This the invention was made with government support under grant number CA171329 awarded by the National Institutes of Health. The Government has certain rights in the invention.

FIELD

The present disclosure is directed to formulations and methods for treatment of disease such as chemoprevention of cancer, for example oral squamous cell carcinoma (OSCC), and for methods of preparing the formulations. Further, the disclosure relates to local administration in slow release dosage forms for treatment of disease. The extended-release formulations are comprised of biodegradable polymeric implants (for example millicylinders and microspheres as well as in situ forming gels) and therapeutic agents selected from an anti-interleukin 6 agent, a synthetic vitamin A analogue and/or metabolite, and/or an estradiol metabolite for the local delivery of therapeutic agents to a site where a cancer has been previously excised or to prevent progression of a precancerous lesion.

BACKGROUND

Oral squamous cell carcinoma (OSCC) is a worldwide health problem associated with significant morbidity and mortality. Five-year survival rates for human papillomavirus-negative OSCCs have only marginally improved over the past 40 years and still hover around 50%. Surgical resection, often accompanied by chemotherapy and/or radiation, is the primary OSCC treatment modality. Following initial therapy, OSCC patients are managed by close clinical follow up often supplemented with imaging (CT, PET or MRI) studies. Despite vigilant monitoring and well-recognized risk factors for recurrence (close margins, immunosuppression, high histologic grade, deep tumor extension), over one third of patients develop life-threatening and often untreatable recurrent OSCCs. Replacement of the current "watchful waiting" strategy with well-tolerated and effective secondary OSCC chemoprevention could make a significant clinical impact for these individuals.

OSCC-directed chemotherapy, much of which is taxol-based and highly toxic, has not been highly successful in OSCC management. To alleviate toxicity issues, tumor-targeted agents were designed to exploit cancers' reliance on overexpressed pathways. While such pathway-targeted therapies may provide initial benefits, signaling redundancies and other compensatory mechanisms ultimately limit efficacy. Sustained activation of the signaling hub and transcription factor Stat3, via feedback loops and/or signaling mutations, is commonly seen in drug resistant cancers. Both mechanistic and clinical data support an IL-6-Stat3-intracrine loop in OSCC pathogenesis. Activated Stat3 initiates expression of numerous tumor-promoting genes including IL-6 (sustained signaling), COX-2 (persistent inflammation), VEGF (angiogenesis) and MMPs (invasion). Reciprocally, IL-6 can induce Stat3 activation, thereby maintaining an intracrine "feed forward" signaling loop. Clinically, Stat3 activation is an early event in OSCC development and is positively associated with a worse prognosis. Similarly, high plasma IL-6 levels in OSCC patients correspond to a more aggressive cancer and poorer prognosis. Notably, NF-κB activation induces a similar panel of tumor-promoting gene expression. Shared functions of these cytosolic signaling hubs-transcription factors may explain the lack of Stat3 inhibitors' clinical efficacy.

The compositions and methods disclosed herein address these and other needs.

SUMMARY

Disclosed herein are novel controlled-release pharmaceutical dosage forms and methods that provide therapeutically effective levels of therapeutic agents directly to a site where a cancer has been previously excised (secondary chemoprevention) or to prevent progression of a precancerous lesion (primary chemoprevention).

These dosage forms are capable of providing therapeutic agents selected from an anti-interleukin 6 agent, a synthetic vitamin A analogue and/or metabolite, and/or an estradiol metabolite in slow release dosage forms for the treatment of disease, including prevention of cancer local recurrence.

In one aspect, disclosed herein is a controlled-release pharmaceutical dosage form comprising: a biodegradable controlled-release polymer, an anti-interleukin 6 agent, and an additional therapeutic agent selected from a synthetic vitamin A analogue and/or metabolite, an estradiol metabolite, or a combination thereof. In one embodiment, the anti-interleukin 6 agent is an anti-interleukin 6 receptor antibody, for example, tocilizumab. In one embodiment, the additional therapeutic agent is a synthetic vitamin A analogue and/or metabolite, for example fenretinide In one embodiment, the additional therapeutic agent is an estradiol metabolite, for example, 2-methoxyestradiol. In a further embodiment, the biodegradable controlled-release polymer comprises poly(lactic-co-glycolic acid).

In one aspect, the controlled-release pharmaceutical dosage form comprises a biodegradable controlled-release polymer, an anti-interleukin 6 agent, a synthetic vitamin A analogue, and/or an estradiol metabolite.

In one embodiment, the therapeutic agents include a synthetic vitamin A analogue or metabolite, an estradiol metabolite, and an anti-IL6 antibody. In one embodiment, the therapeutic agents include fenretinide (4-HPR), 2-methoxyestradiol (2-ME), and tocilizumab (TOC). In one embodiment, the therapeutic agents are delivered in a controlled release fashion using an in situ forming gel or a polylactide-coglycolide (PLGA) millicylinder.

In another aspect, disclosed herein is a method of primary chemoprevention comprising: administering to a host a controlled-release pharmaceutical dosage form in an amount sufficient to inhibit the progression of the precancerous lesion to a cancer; wherein the controlled-release pharmaceutical dosage form comprises a biodegradable controlled-release polymer, an anti-interleukin 6 agent, and an additional therapeutic agent selected from a synthetic vitamin A analogue and/or metabolite, an estradiol metabolite, or a combination thereof.

In yet another aspect of the invention, provided herein is a method of secondary chemoprevention comprising: administering to a host a controlled-release pharmaceutical dosage form in an amount sufficient to prevent the recurrence of a cancer comprising; wherein the controlled-release pharmaceutical dosage form comprises a biodegradable controlled-release polymer, an anti-interleukin 6 agent, and an additional therapeutic agent selected from a synthetic vitamin A analogue, an estradiol metabolite, or a combination thereof.

In one aspect, the methods described herein are used to prevent recurrence of a solid tumor. In one embodiment, the cancer is selected from oral squamous cell carcinoma (OSCC), prostate cancer, or breast cancer.

BRIEF DESCRIPTION OF THE DRAWINGS

The accompanying figures, which are incorporated in and constitute a part of this specification, illustrate several aspects described below.

FIGS. 1C and 1D show the proteome profiles and cell line specific cytokine release. Conditioned media from 24 hour sera-deprived JSCC cell lines were analyzed to determine extent of autologous cytokine release. Cytokines uniformly released by all cell lines were: Dickkofp-1, IL-8, and macrophage inhibitory factor. Only the Afatinib and Vargatef refractory JSCC1 and JSCC2 cell lines released the proangiogenic proteins angiogenin, CXCL1, and PDGF-AA. Notably, Vargatef does not block PDGF-AA signaling.

FIG. 1E shows the inter-cell line heterogeneity extends to OSCC-relevant cytokine release. To provide more quantitative assessments, ELISA analyses were conducted to assess autologous production and release of three OSCC-relevant cytokines i.e. IL-6, VEGF, EGF and TNFα from 24 hour sera-deprived cells (n=9 for every cell line, mean±s.e.m. pg/$10^6$ cells). None of the lines released detectable levels of epidermal growth factor (assay level of detection 3.9 pg/ml), with only released low levels of TGFα. Inter-cell line comparisons of IL-6 and VEGF release revealed significant differences (Kruskal Wallis followed by a Dunn's Multiple Comparison post hoc test, =p<0.01, **=p<0.0001).

DETAILED DESCRIPTION

Figure 1A:
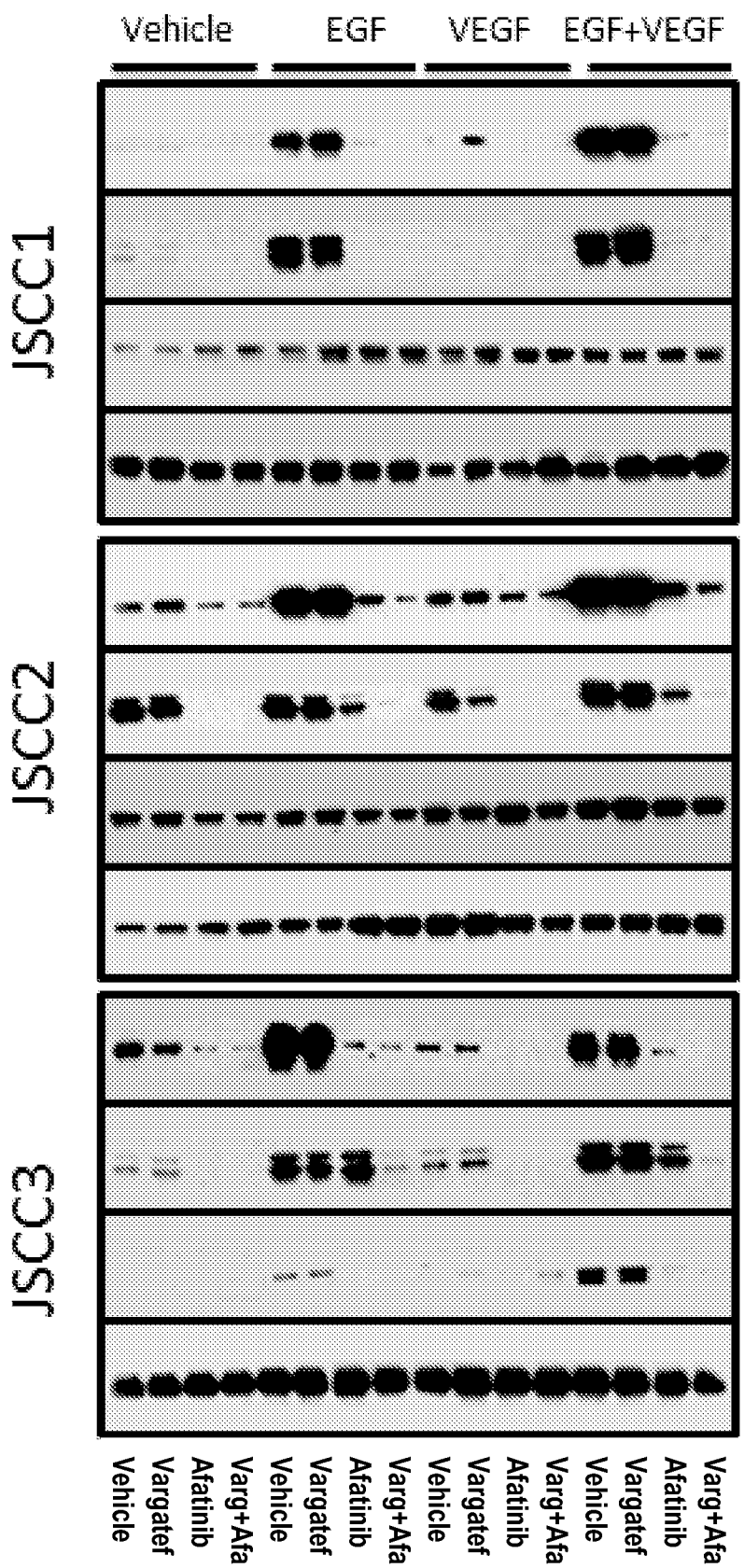
FIGS. 1A and 1B show the effects of Afatinib and Vargatef on OSCC intracellular signaling. Cells were cultured for 24 h in sera free base medium, followed by a 1 hour pretreatment with Afatinib (100 nM) and/or Vargatef (100 nM) followed by a 20 minute stimulation with EGF (50 ng/ml) and/or VEGF (50 ng/ml) prior to harvesting. The extent of constitutive signaling (vehicle lane) was cell line dependent. JSCC2 cells showed the highest baseline signaling (constitutive pERK1/2 and pSTAT3), while JSCC1 and JSCC3 cells showed modest constitutive pSTAT3 and pERK1/2 activation, respectively. Growth factor challenge (50 ng/ml both EGF and VEGF singularly and in combination) increased receptor and downstream signaling activity with VEGF inducing some crossover EGFR activation. While Afatinib and Vargatef blocked STAT3 phosphorylation in the JSCC3 cells, pSTAT3 persisted in the JSCC1 and JSCC2 cell lines regardless of treatment. The accompanying histogram depicts levels of phosphorylated ERKR, ERK1/2 and STAT3 relative to GAPDH.

Disclosed herein are novel controlled-release pharmaceutical dosage forms and methods that provide therapeutically effective levels of therapeutic agents directly to a site where a cancer has been previously excised (secondary chemoprevention) or to prevent progression of a precancerous lesion (primary chemoprevention).

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

As used in the specification and claims, the singular form "a," "an," and "the" include plural references unless the context clearly dictates otherwise. For example, the term "a cell" includes a plurality of cells, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition (e.g., cancer). The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

As used herein, the terms "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount." However, an appropriate "effective" amount in any subject case may be determined by one of ordinary skill in the art using routine experimentation. Also, as used herein, and unless specifically stated otherwise, an "effective amount" of a beneficial agent can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject.

The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

As used herein, the term "mixture" can include solutions in which the components of the mixture are completely miscible, as well as suspensions and emulsions, in which the components of the mixture are not completely miscible.

As used herein, the term "subject" can refer to living organisms such as mammals, including, but not limited to humans, livestock, dogs, cats, and other mammals. Administration of the therapeutic agents can be carried out at dosages and for periods of time effective for treatment of a subject. In some embodiments, the subject is a human. In some embodiments, the pharmacokinetic profiles of the systems of the present disclosure are similar for male and female subjects.

As used herein, the term "controlled-release" or "controlled-release drug delivery" refers to release or administration of a drug from a given dosage form in a controlled fashion in order to achieve the desired pharmacokinetic profile in vivo. An aspect of "controlled" drug delivery is the ability to manipulate the formulation and/or dosage form in order to establish the desired kinetics of drug release.

The phrases "concurrent administration", "administration in combination", "simultaneous administration" or "administered simultaneously" as used herein, means that the compounds are administered at the same point in time or immediately following one another. In the latter case, the two compounds are administered at times sufficiently close that the results observed are indistinguishable from those achieved when the compounds are administered at the same point in time.

Controlled-Release Pharmaceutical Dosage Forms

In one aspect, disclosed herein is a controlled-release pharmaceutical dosage form comprising: a biodegradable controlled-release polymer, an anti-interleukin 6 agent, and an additional therapeutic agent selected from a synthetic vitamin A analogue and/or metabolite, an estradiol metabolite, or a combination thereof.

In one aspect, disclosed herein is a controlled-release pharmaceutical dosage form comprising: a biodegradable controlled-release polymer, an anti-interleukin 6 agent, and an additional therapeutic agent selected from a synthetic vitamin A analogue or an estradiol metabolite.

In another aspect, disclosed herein is a controlled-release pharmaceutical dosage form comprising: a biodegradable controlled-release polymer, an anti-interleukin 6 agent, a synthetic vitamin A analogue or metabolite, and an estradiol metabolite.

In one embodiment, the anti-interleukin 6 agent is an anti-interleukin 6 receptor antibody, for example, tocilizumab. In one embodiment, the additional therapeutic agent is a synthetic vitamin A analogue, for example fenretinide. In one embodiment, the additional therapeutic agent is an estradiol metabolite, for example, 2-methoxyestradiol. In a further embodiment, the biodegradable controlled-release polymer comprises poly(lactic-co-glycolic acid).

In one aspect, the controlled-release pharmaceutical dosage form comprises a biodegradable controlled-release polymer, an anti-interleukin 6 agent, a synthetic vitamin A analogue and/or metabolite, and/or an estradiol metabolite. In one embodiment, the therapeutic agents include a vitamin A analogue, an estradiol metabolite, and an anti-IL6 antibody. In one embodiment, the therapeutic agents include fenretinide (4-HPR), 2-methoxyestradiol (2-ME), and/or tocilizumab (TOC). In one embodiment, the therapeutic agents are delivered in a controlled release fashion using an in situ forming gel or a polyactide-coglycolide (PLGA) millicylinder.

In one embodiment, disclosed herein is a controlled-release pharmaceutical dosage form comprising: a biodegradable controlled-release polymer, fenretinide (4-HPR), 2-methoxyestradiol (2-ME), and tocilizumab (TOC).

In one embodiment, the controlled-release pharmaceutical dosage form is delivered by local injection. In one embodiment, the controlled-release pharmaceutical dosage form is delivered with a trocar.

In one embodiment, the formulation comprises a multi-drug biodegradable local controlled release dosage forms for fenretinide, 2-methoxyestradiol (2-ME), and tocilizumab (TOC). In one embodiment, there is >5-10% drug loading, low initial burst (<20%) and 1-month continuous release of stable drug. Copolymers derived from lactic and glycolic acids (PLGAs) are commonly used biodegradable polymer for long-term delivery of drugs over weeks to months, and are in use in more than a dozen commercial products. These products deliver small molecules, including steroids such as dexamethasone, peptides such as exenatide (glucagon peptide-1 agonist), and proteins such as growth hormone.

There are three injectable PLGA configurations commonly used clinically: (a) microspheres (~10-100 µm), (b) millicylinders (~0.5-1.5 mm), and (c) in-situ forming gels, which are drug/PLGA/organic solvent mixtures that solidify upon injection in vivo. Millicylinders can offer distinct advantages in terms of reduced initial burst release of drug in the first day after administration and increased protein stability. The cylindrical geometry allows local controlled release of multiple drugs from one dosage form, which allows easy administration and controlled-release drug delivery of multiple drugs from a single location. Microspheres and in-situ forming gels can be more susceptible to high initial burst release because of the small diffusion pathlengths and the rapid extraction of the water-miscible organic solvent after administration, respectively.

In one embodiment, the biodegradable controlled-release polymer is selected from poly(lactides), poly(glycolides), poly(lactide-co-glycolides), poly(lactic-acid)s, poly(glycolic acid)s, poly(lactic acid-co-glycolic acid)s, poly(hydroxymethyl glycolide-co-lactide), polycaprolactone, polycarbonates, polyesteramides, polyanhydrides, poly(amino acids), polyorthoesters, polycyanoacrylates, poly(p-dioxanone), poly(alkylene oxalate)s, biodegradable polyurethanes, homopolymers, copolymers, and blended polymers. In one embodiment, the biodegradable controlled-release polymer comprises poly(lactic-co-glycolic acid) (PLGA). PLGA polymers have been used extensively in microspheres, millicylindrical rods, coatings and various other devices, and their rates of degradation and biocompatibility are well understood.

In one example, the microencapsulation can be done by solvent extrusion. 4-HPR powder can be ground and sieved (<90 µm), combined with excipients and suspended in an acetone solution of poly(D,L-lactic-co-glycolic acid) (PLGA), acid-capped, MW 13-24 kDa. The suspension is extruded with a syringe into silicone rubber tubing before drying under vacuum. This polymer provides 4-6 week sustained polymer erosion and typically releases drugs without a lag time, commonly observed with higher molecular weight PLGAs and drug load is typically 10-50%. Solubilizers for co-encapsulation can include deoxycholate salts, Pluronic F127, Brij 35, and β-cyclodextrin.

Drug loading can be determined by HPLC after extraction with THF/ethanol. In vitro release can be determined at 37°

C. under perfect sink conditions using PBS+0.084% Tween 80, which provides the same fenretinide solubility (21 µg/mL) as found in bovine serum.

In one embodiment, 2-ME in PLGA can maximize drug loading and facilitate continuous release of the steroid over the correct time scale of release in vivo. Maximizing drug loading can provide more flexibility for dosing and increase the probability of attaining local therapeutic levels. IN one embodiment, the steroid is slowly and continuously released for >1 month in vitro from two different low molecular weight acid-capped PLGA 50/50s at 10% 2-ME loading. The drug release could also be strongly increased by numerous additives (for example β-cyclodextrin, Pluronic F127, or PEG8000) to affect the drug solubility and/or pore formation of the polymer throughout the release period.

2-ME with/without excipients can be combined with acid-capped PLGA 50/50 (13-24 kD) in acetone and extruded. Drug loading is typically about 10-50%. Drug loading can be determined by HPLC after dissolving implants in acetonitrile. Release kinetics in vitro can be performed in PBS+0.02% Tween 80 (PBST) at 37° C. under perfect sink conditions with HPLC detection.

The anti-IL-6 receptor IgG1κ monoclonal antibody (MAb), tocilizumab (TOC) can also be formulated in PLGA. This can increase the (1) stability of the protein and (2) manage the elevated level of small molecule excipients necessary to stabilize the protein. The millicylindrical configuration can provide distinct protein stability advantages owing to: (1) the encapsulation is anhydrous, which allows the protein to avoid contact the organic solvent while in the solution state, which in turn minimizes protein unfolding and aggregation as often occurs at water-organic solvent interfaces; and (2) the larger configuration only requires solid protein particles for encapsulation <90 µm, and therefore, avoids the extensive (and sometimes damaging) micronization of the protein (necessary for microspheres). To inhibit the pH drop resulting from a build-up of acidic degradation products during biodegradation of the PLGA polyester (i.e., each ester bond cleaved produces one new carboxylic acid), a poorly soluble base such as $Mg(OH)_2$ and $MgCO_3$ can successfully manage the lower microclimate pH over a sufficient time window to allow the protein to be safely released from the polymer.

TOC is currently available in two different formulations, in solution for IV infusion and SC injection, both of which contain multiple stabilizing small molecules to maintain the shelf life of the product. These small molecules when encapsulated in PLGA can give rise to significant osmotic pressures, making it difficult to avoid all the protein from coming out immediately after administration.

The components of Actemra® solution containing TOC can be exchanged into histidine buffer pH 6 before adjustment of excipient content before freeze-drying. The solid can then be ground with a CryoMill before sieving through 90-µm screen. The solid powder can be suspended at 10% TOC theoretical loading in PLGA 50/50 end-capped (Mw~60 kD)+3% $MgCO_3$/acetone solution and extruded into silicone rubber before ambient and vacuum drying (40° C.). For coated implants, the core implants can be placed back into silicone tubing and blank PLGA solution in acetone can be extruded over the core implants to coat before drying.

For determination of MAb loading, the polymer can be dissolved first in acetone to remove the polymer without dissolving the protein. After repeating 3× and evaporation of the solvent, the protein is reconstituted in aqueous solution and assayed by both size exclusion chromatography (SEC) and sandwich ELISA (AbD Serotec), and other structural assays as needed. In vitro release can be conducted at 37° C. in PBST as for 2-ME, except analysis can be by SEC and ELISA. Although ELISA is expected to mimic Mab native structure, higher order structural analysis of TOC can be performed using circular dichroism and fluorescence spectroscopy.

For 2-ME and TOC, in vivo release can be commenced once formulations are obtained based on in vitro analysis (i.e., >5-10% loading, <20% 1-day initial burst release, continuous release of 80% over 1 month of stable drug). To characterize implant release in test formulations of poly (lactic-co-glycolic) (PLGA) millicylinders in vivo, 120 7-week old female Sprague Dawley rats are used. Each rat can receive 6 implants. Each formulation is tested in triplicate.

All millicylinder implants can be chemically analyzed and weighed prior to implantation. Following euthanasia at the aforementioned time points, implants removed for analyses, implant site tissues snap frozen for cryosection and tissue distribution for drug release and diffusion studies-2-ME and 4-HPR (LCMS), TOC (ELISA). Stability analysis can also be performed on the extracted agents to confirm stability in vivo, i.e., LCMS for 4-HPR and 2-ME & SEC/ELISA & structural analyses for TOC.

In one embodiment, the therapeutic agents are combined into a contiguous implant by placing the segments back into the silicone rubber mold with a small drop of polymer solution to fuse the PLGA segments upon drying. The in vitro and in vivo (SC rats) release for each drug can then be confirmed.

In one aspect, an effective amount of an active compound as described herein is incorporated microspheres. The microspheres can include, by way of example, glass, ceramic, metal, plastic, or mixtures thereof. In some embodiments, the dosage form comprises a shell and can include a layer of microspheres surrounding the payload and a polymer layer surrounding the layer of microspheres, while in other embodiments, the shell can include multiple payloads (each surrounded by a layer of microspheres) that are agglomerated within a polymer matrix. In any of the above embodiments, the shell can include a layer that is a mixture of microspheres and polymer. See US2015/0164805 (hereby incorporated by reference) for additional discussion of drug delivery using microspheres.

In another aspect, an effective amount of an active compound as described herein is incorporated into nanoparticles, e.g. for convenience of delivery and/or extended release delivery. The use of materials in nanoscale provides one the ability to modify fundamental physical properties such as solubility, diffusivity, blood circulation half-life, drug release characteristics, and immunogenicity. In the last two decades, a number of nanoparticle-based therapeutic and diagnostic agents have been developed for the treatment of cancer, diabetes, pain, asthma, allergy, and infections. These nanoscale agents can provide more effective and/or more convenient routes of administration, lower therapeutic toxicity, extend the product life cycle, and ultimately reduce health-care costs. As therapeutic delivery systems, nanoparticles allow targeted delivery and controlled release.

In addition, nanoparticle-based drug delivery can be used to release drugs at a sustained rate and thus lower the frequency of administration, deliver drugs in. a target manner to minimize systemic side effects, or deliver two or more drugs simultaneously for combination therapy to generate a synergistic effect and suppress drug resistance. To date, a number of nanotechnology-based therapeutic products have been approved for clinical use. Among these products, liposomal drugs and polymer-based conjugates account for more than 80% of the products. See, Zhang, L., et al., Nanoparticles in Medicine: Therapeutic Applications and Developments, Clin. Pharm. and Ther., 83(5):761-769, 2008.

Nanoparticles may be prepared using a wide variety of methods known in the art. For example, nanoparticles can be formed by methods as nanoprecipitation, flow focusing fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanomaterials have been described (Pellegrino et al., 2005, Small, 1 :48; Murray et al., 2000, Ann. Rev. Mat. Sci; 30:545; and Trindade et al., 2001, Chem. Mat., 13:3843). Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6): 843-853 (2010)).

In some embodiments, the compounds described herein are associated with a nanoparticle or microsphere (such as a polymeric nanoparticle or polymeric microsphere). Nanoparticles and microspheres may comprise natural polymers, including but not limited to chitosan, alginate, dextran, gelatin, and albumin, and synthetic polymers such as, but not limited to, poly(lactide-co-glycolide) (PLGA), (3-hydroxybutyrate-co-3-hydroxyvalerate) (PHBV), poly(sebacic anhydride), poly(e-caprolactone), polystyrene, thermoresponsive (i.e., NIPAAm and CMCTS-g-PDEA) and pH-responsive (i.e., Eudragit LI 00, Eudragit S and AQOAT AS-MG) polymers.

In one embodiment, the polymeric particle is between about 0.1 nm to about 10000 nm, between about 1 nm to about 1000 nm, between about 10 nm and 1000 nm, between about 100 nm and 800 nm, between about 400 nm and 600 nm, or about 500 nm. In one embodiment, the microparticles are about 0.1 nm, 0.5 nm, 1.0 nm, 5.0 nm, 10 nm, 25 nm, 50 nm, 75 nm, 100 nm, 150 nm, 200 nm, 250 nm, 300 nm, 400 nm, 450 nm, 500 nm, 550 nm, 600 nm, 650 nm, 700 nm, 750 nm, 800 nm, 850 nm, 900 nm, 950 nm, 1000 nm, 1250 nm, 1500 nm, 1750 nm, or 2000 nm.

In one embodiment, the polymeric particle is between about 1 µm to about 1000 µm or between about 10 µm to about 100 µm. In one embodiment, the micro-spheres are about 1 µm, 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, or 1000 µm.

In one embodiment, the compounds described herein are covalently coupled to a polystyrene particle, PLGA particle, PLA particle, or other microsphere or nanoparticle.

In one aspect, disclosed herein is a controlled-release implant that maintains therapeutic drug levels over time for treatment of disease that is comprised of: a biodegradable controlled-release polymer, an anti-interleukin 6 agent, and an additional therapeutic agent selected from a synthetic vitamin A analogue and/or metabolite, an estradiol metabolite, or a combination thereof. In one embodiment, the anti-interleukin 6 agent is an anti-interleukin 6 receptor antibody, for example, tocilizumab. In one embodiment, the additional therapeutic agent is a synthetic vitamin A analogue, for example fenretinide. In one embodiment, the additional therapeutic agent is an estradiol metabolite, for example, 2-methoxyestradiol. In a further embodiment, the biodegradable controlled-release polymer comprises poly (lactic-co-glycolic acid).

In one aspect, the controlled-release pharmaceutical dosage form comprises a biodegradable controlled-release polymer, an anti-interleukin 6 agent, a synthetic vitamin A analogue and/or metabolite, and/or an estradiol metabolite (singularly or in combination). For example, slow release injectable dosage forms of tocilizumab can be used for the management of rheumatoid arthritis. This would decrease the number of injections patients have to receive and also provide a more sustained anti-inflammatory profile.

In one embodiment, the therapeutic agents include a synthetic vitamin A analogue, an estradiol metabolite, and an anti-IL6 antibody. In one embodiment, the therapeutic agents include fenretinide (4-HPR), 2-methoxyestradiol (2-ME), and tocilizumab (TOC). In one embodiment, the therapeutic agents are delivered in a controlled release fashion using an in situ forming gel, a polyactide-coglycolide (PLGA) millicylinder or microsphere.

An important consideration is the pharmacologic advantage that is provided by controlled release local delivery vehicles. Such a delivery approach avoids peaks and valleys common with other dosage forms such as pills or topical gels. In addition controlled release local delivery formulations can provide effective drug levels at the treatment site without inducing toxicity away from the treatment sites. This strategy helps eliminate deleterious systemic effects associated with pill or intravenous doing forms.

Therapeutic Agents

Vitamin A Analogues and Metabolites

In one aspect, the therapeutic agent is a synthetic Vitamin A analogue, such as retinide compositions. In a particular embodiment, the system includes a formulation that is especially useful for the delivery of retinide compositions. In certain embodiments, the retinide composition comprises a synthetic retinoid such as fenretinide. Fenretinide (4-hydroxy(phenyl)retinamide) is a highly lipophilic drug and has a log P of 8.03, which results in minimal buccal mucosal uptake and permeation.

Previous problems with systemic fenretinide delivery for OSCC chemoprevention include inactivation by methylation in the liver. The local delivery from a polymeric implant system can provide therapeutic fenretinide level directly at the treatment site, thereby improving the therapeutic efficacy of fenretinide in cancer chemoprevention. However, fenretinide is a highly hydrophobic drug with very low water solubility (below HPLC detection limit).

Various vitamin A retinoids that can be used as a therapeutic agent include, for example, all-trans-retinoic acid, 13-cis-retinoic acid, beta-carotene, isotretinoin or eletrinate. In addition, synthetic vitamin A metabolites such as 4-oxo-fenretinide can also be used.

Estradiol Derivatives and Metabolites

2-Methoxyestradiol (2-ME), a metabolite of 17-β-estradiol, inhibits tumor growth, neovascularization, and growth of cancer cells (angiosarcoma, gastric, cervical, colorectal, hepatocellular, prostate, lung, pancreatic, breast, neuroblastoma, leukemia, multiple myeloma). In addition to inhibiting the proliferation of cancer cells, 2-ME also possesses anti-angiogenic properties. 2-ME induces changes in the levels and activities of many proteins involved in regulation of the cell cycle, including stress kinases, cell division kinases, cyclin B, and regulators of cell cycle arrest and apoptosis. 2-ME has been shown to inhibit growth of ER+ and ER− breast cancer cell lines and HeLa cells. In prostate cancer, 2-ME acts through the modulation of the expression of androgen-regulated genes, mainly by reducing the levels of TSG-6 immunoreactivity. Because of its efficacy in murine tumor models, 2-ME is being evaluated in Phase I and Phase II clinical trials against a variety of human tumors.

In one embodiment, one of the therapeutic agent comprises an estradiol metabolite. In one embodiment, the estradiol metabolite is selected from the group consisting of a catecholestradiol and a methoxyestradiol. In one embodiment, the estradiol metabolite is selected from the group consisting of 2-hydroxyestradiol, 2-methoxyestradiol, 4-hydroxyestradiol and 4-methoxyestradiol. In one particular embodiment, the estradiol metabolite is 2-methoxyestradiol.

Anti-Interleukin-6 Agents

Interleukin 6 is a cytokine that plays a role in many inflammatory diseases and cancers. The first FDA approved anti-interleukin-6 agent is tocilizumab (Actemra), which is an antibody against the IL6 receptor. An additional approved antibody is situximab (Sylvant). Additional anti-interleukin-6 agents include, but are not limited to, sarilumab, olokizumab, elsilimomab, BMS-945429, sirukumab, and CPSI-2364.

In one embodiment, the anti-interleukin-6 agent is an interleukin-6 receptor inhibitor. In one embodiment, the anti-interleukin-6 agent is an anti-interleukin-6 receptor antibody. In a particular embodiment, the anti-interleukin-6 receptor antibody is tocilizumab.

Patents and patent publications related to anti-IL-6R antibodies include, for example: U.S. Pat. No. 5,171,840 (Kishimoto), U.S. Pat. No. 5,480,796 (Kishimoto), U.S. Pat. No. 5,670,373 (Kishimoto), U.S. Pat. No. 5,851,793 (Kishimoto), U.S. Pat. No. 5,990,282 (Kishimoto), U.S. Pat. No. 6,410,691 (Kishimoto), U.S. Pat. No. 6,428,979 (Kishimoto), U.S. Pat. No. 5,795,965 (Tsuchiya et al.), U.S. Pat. No. 5,817,790 (Tsuchiya et al.), U.S. Pat. No. 7,479,543 (Tsuchiya et al.), US 2005/0142635 (Tsuchiya et al.), U.S. Pat. No. 5,888,510 (Kishimoto et al.), US 2001/0001663 (Kishimoto et al.), US 2007/0036785 (Kishimoto et al.), U.S. Pat. No. 6,086,874 (Yoshida et al.), U.S. Pat. No. 6,261,560 (Tsujinaka et al.), U.S. Pat. No. 6,692,742 (Nakamura et al.), U.S. Pat. No. 7,566,453 (Nakamura et al.), U.S. Pat. No. 7,771,723 (Nakamura et al.), US 2002/0131967 (Nakamura et al.), US 2004/0247621 (Nakamura et al.), US 2002/0187150 (Mihara et al.), US 2005/0238644 (Mihara et al.), US 2009/0022719 (Mihara et al.), US 2006/0134113 (Mihara), U.S. Pat. No. 6,723,319 (Ito et al.), U.S. Pat. No. 7,824,674 (Ito et al.), US 2004/0071706 (Ito et al.), U.S. Pat. No. 6,537,782 (Shibuya et al.), U.S. Pat. No. 6,962,812 (Shibuya et al.), WO 00/10607 (Akihiro et al.), US 2003/0190316 (Kakuta et al.), US 2003/0096372 (Shibuya et al.), U.S. Pat. No. 7,320,792 (Ito et al.), US 2008/0124325 (Ito et al.), US 2004/0028681 (Ito et al.), US 2008/0124325 (Ito et al.), US 2006/0292147 (Yoshizaki et al.), US 2007/0243189 (Yoshizaki et al.), US 2004/0115197 (Yoshizaki et al.), US 2007/0148169 (Yoshizaki et al.), U.S. Pat. No. 7,332,289 (Takeda et al.), U.S. Pat. No. 7,927,815 (Takeda et al.), U.S. Pat. No. 7,955,598 (Yoshizaki et al.), US 2004/0138424 (Takeda et al.), US 2008/0255342 (Takeda et al.), US 2005/0118163 (Mizushima et al.), US 2005/0214278 (Kakuta et al.), US 2008/0306247 (Mizushima et al.), US 2009/0131639 (Kakuta et al.), US 2006/0142549 (Takeda et al.), U.S. Pat. No. 7,521,052 (Okuda et al.), US 2009/0181029 (Okuda et al.), US 2006/0251653 (Okuda et al.), US 2009/0181029 (Okuda et al.), US 2007/0134242 (Nishimoto et al.), US 2008/0274106 (Nishimoto et al.), US 2007/0098714 (Nishimoto et al.), US 2010/0247523 (Kano et al.), US 2006/0165696 (Okano et al.), US 2008/0124761 (Goto et al.), US 2009/0220499 (Yasunami), US 2009/0220500 (Kobara), US 2009/0263384 (Okada et al.), US 2009/0291076 (Morichika et al.), US 2009/0269335 (Nakashima et al.), US 2010/0034811 (Ishida), US 2010/0008907 (Nishimoto et al.), US 2010/0061986 (Takahashi et al.), US 2010/0129355 (Ohguro et al.), US 2010/0255007 (Mihara et al.), US 2010/0304400 (Stubenrach et al.), US 2010/0285011 (Imaeda et al.), US 2011/0150869 (Mitsunaga et al.), WO 2011/013786 (Maeda) and US 2011/0117087 (Franze et al).

Delivery of these IL-6 inhibitors from an implant (for example, PLGA) would be superior to weekly injections in the joints. In addition, sustained drug delivery can provide improved efficacy. Another major advantage is that systemically delivered IL-6 inhibitors have a major side effect i.e. immunsuppression. Patients that use tocilizumab systemically are much more susceptible to cancers such as lymphoma. Therefore, local delivery would eliminate this concern.

Cancers and Solid Tumors

The active compounds and methods described herein are useful for the prevention of recurrence of excised solid tumors. In one embodiment, the cancer recurrence to be prevented is selected from oral squamous cell carcinoma (OSCC), breast cancer, prostate cancer, or cervical cancer. In one embodiment, the cancer recurrence to be prevented is oral squamous cell carcinoma (OSCC). In another embodiment, the cancer recurrence to be prevented is breast cancer. In a further embodiment, the cancer recurrence to be prevented is prostate cancer. In one embodiment, the cancer recurrence to be prevented is cervical cancer.

In one aspect, the methods described herein are used to prevent solid tumor recurrence, for example, breast cancer (including ductal carcinoma, lobular carcinoma, inflammatory breast cancer, clear cell carcinoma, mucinous carcinoma, serosal cavities breast carcinoma); prostate cancer; prostate adenocarcinoma; cancer of the head and neck (including squamous cell carcinomas); or cervical cancer.

In some embodiments, the cancer is a tissue limited cancer. In one embodiment, the cancer comprises a high Stat3-IL6 driven phenotype.

Methods of Treatment

In one aspect, disclosed herein is a method of primary chemoprevention comprising: administering to a host a controlled-release pharmaceutical dosage form in an amount sufficient to inhibit the progression of the precancerous lesion to a cancer; wherein the controlled-release pharmaceutical dosage form comprises a biodegradable controlled-release polymer, an anti-interleukin 6 agent, and an additional therapeutic agent selected from a synthetic vitamin A analogue and/or metabolite, an estradiol metabolite, or a combination thereof.

In another aspect, disclosed herein is a method of primary chemoprevention comprising: administering to a host a controlled-release pharmaceutical dosage form in an amount sufficient to inhibit the progression of the precancerous lesion to a cancer; wherein the controlled-release pharmaceutical dosage form comprises a biodegradable controlled-release polymer, an anti-interleukin 6 agent, and an additional therapeutic agent selected from a synthetic vitamin A analogue or an estradiol metabolite.

In a further aspect of the invention, provided herein is a method of secondary chemoprevention comprising: administering to a host a controlled-release pharmaceutical dosage form in an amount sufficient to prevent the recurrence of a cancer comprising; wherein the controlled-release pharmaceutical dosage form comprises a biodegradable controlled-release polymer, an anti-interleukin 6 agent, and an additional therapeutic agent selected from a synthetic vitamin A analogue and/or metabolite, an estradiol metabolite, or a combination thereof.

In yet another aspect of the invention, provided herein is a method of secondary chemoprevention comprising: administering to a host a controlled-release pharmaceutical dosage form in an amount sufficient to prevent the recurrence of a cancer comprising; wherein the controlled-release pharmaceutical dosage form comprises a biodegradable controlled-release polymer, an anti-interleukin 6 agent, and an additional therapeutic agent selected from a synthetic vitamin A analogue or an estradiol metabolite.

In one embodiment, the method comprises administering an anti-interleukin 6 agent is an anti-interleukin 6 receptor antibody, for example, tocilizumab. In one embodiment, the additional therapeutic agent is a synthetic vitamin A analogue and/or metabolite, for example fenretinide In one embodiment, the additional therapeutic agent is an estradiol metabolite, for example, 2-methoxyestradiol. In a further embodiment, the biodegradable controlled-release polymer comprises poly(lactic-co-glycolic acid).

In some embodiment, the methods described herein are used as chemoprevention for premalignant lesions either de novo (primary chemoprevention) or to prevent recurrence (secondary chemoprevention) of a solid tumor.

In one embodiment, the cancer is selected from oral squamous cell carcinoma (OSCC), prostate cancer, or breast cancer. In one embodiment, the cancer is oral squamous cell carcinoma (OSCC). In one embodiment, the cancer is selected from prostate cancer. In one embodiment, the cancer is breast cancer.

In one embodiment, the present disclosure provides a method of treating or preventing arthritis comprising: administering to a host a controlled-release pharmaceutical dosage form; wherein the controlled-release pharmaceutical dosage form comprises a biodegradable controlled-release polymer, an anti-interleukin 6 agent, and/or an additional therapeutic agent selected from a synthetic vitamin A analogue, an estradiol metabolite, or a combination thereof.

In one embodiment, the present disclosure provides a method of treating or preventing arthritis comprising: administering to a host a controlled-release pharmaceutical dosage form; wherein the controlled-release pharmaceutical dosage form comprises a biodegradable controlled-release polymer, an anti-interleukin 6 agent, and/or an additional therapeutic agent selected from a synthetic vitamin A analogue or an estradiol metabolite. In one embodiment, the arthritis is rheumatoid arthritis. In one embodiment, the arthritis is juvenile arthritis.

EXAMPLES

The following examples are set forth below to illustrate the compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Benefits of Multifaceted Chemopreventives in the Suppression of the Oral Squamous Cell Carcinoma (OSCC) Tumorigenic Phenotype Five-year survival rates for human papillomavirus-negative oral squamous cell carcinoma OSCCs have only marginally improved over the past 40 years and still hover around 50% [1]. Following management of the primary OSCC tumor (surgical resection often accompanied by radiation and/or chemotherapy) patients are managed by close clinical follow up supplemented with CT, PET, or MRI imaging. Despite vigilant monitoring and well-recognized risk factors for recurrence (close margins, immunosuppression, high histologic grade, deep tumor extension) over one third of patients develop life-threatening and often untreatable recurrent OSCCs [2, 3]. Replacement of this "watchful waiting" strategy with a well-tolerated and effective strategy to prevent OSCC recurrence (secondary chemoprevention) could benefit patients.

In an effort to reduce toxicities and bystander effects, cancer drugs have been designed to exploit cancers' dependence on overexpressed receptors and signaling pathways [4-9]. While conceptually appealing, the collective clinical data from small molecule receptor antagonists and tyrosine kinase inhibitors have been disappointing [8-10]. The EGFR chimeric monoclonal antibody, cetuximab, was ineffective both as monotherapy and also when combined with platinum-based chemoradiation in patients with advanced OSCC [8]. Small molecular tyrosine kinase receptor inhibitors e.g. EGFR family, VEGF and combinations thereof e.g. Vandetanib have also been ineffective [9]. A recent dose escalation trial to evaluate combined Afatinib (EGFR tyrosine kinase inhibitor) and Vargatef (inhibits VEGFR, PDGFR and FGFR tyrosine kinases) treatment on advanced solid tumors resulted in high rates of disease progression and other trial-terminating severe adverse events [10].

Related cancer-targeted drugs have also been developed to blockade downstream signaling hubs such as STAT3 [11]. STAT3, which is activated in many solid tumors including OSCC, upregulates transcription of several cancer-relevant genes including COX-2, IL-6, VEGF, MMPs and can silence genes by DNA methylation [12,13,14]. STAT3 in conjunction with IL-6 participates in an intracrine "feed forward" loop made possible by IL-6's reciprocal activation of STAT3 [13]. High OSCC tumor levels of IL-6 positively correlate with elevated intratumor pSTAT3 levels and a worse prognosis including higher rates of regional and distant metastases [15]. Furthermore, OSCC recurrences are accompanied by elevated serologic levels of IL-6, along with C-reactive protein and serum amyloid [16]. While STAT3 blockade should theoretically abate effects of inappropriately sustained upstream signaling pathways, STAT3 inhibitor trials closed early due to disease progression [17, 18]. Notably, the referenced studies employed the targeted drugs as chemotherapeutics in advanced clinical stage cohorts [6-10, 17, 18]. Their collective results showed that while targeted treatment may be effective initially, signaling redundancies and other compensatory mechanisms ultimately limit efficacy [9, 19]. In contrast, secondary OSCC chemoprevention in a relatively healthy patient cohort requires a distinctive strategy i.e. one that is effective long term and capable of addressing multiple growth perturbations without marked toxicities.

As opposed to targeted drugs, chemopreventives possess multiple mechanisms of action which include growth state regulation, inhibition of angiogenesis, and suppression of signaling cascades [20]. It was recently shown that fenretinide binds to and perturbs two proteins i.e. FAK and PYK2 essential for signaling and OSCC-ECM interactions including invasion [21]. This current example evaluated the abilities of three chemopreventives i.e. the vitamin A analogue fenretinide (4-HPR), the estrogen metabolite 2-methoxyestradiol (2-ME) and the humanized monoclonal antibody to the IL-6R receptor tocilizumab (TOC) to modulate OSCC cell gratuitous signaling and tumorigenesis. These agents possess complementary mechanisms of action that include induction of apoptosis (4-HPR, 2-ME) and differentiation (4-HPR), capacity to inhibit intracellular signaling proteins and invasion (4-HPR) and reduce IL-6-mediated signaling (TOC) [15, 21-25]. Corresponding studies on OSCC tumors (from which cell lines were isolated) provided corresponding in situ data while molecular modeling studies depicted 4-HPR-cell target interactions. These results show that while monotherapy provides therapeutic benefits, chemopreventive combinations provide enhanced in vitro and in vivo efficacy.

Materials and Methods

Cell Isolation, Validation, Culture and Characterization.

OSCC tumor, perilesional and metastatic tissues and corresponding cell lines (fresh tumor tissue derived) were obtained in accordance with Ohio State University Institutional Review Board approval. JSCC-1, JSCC-2, and JSCC-3 cells which were isolated from OSCCs of tonsil, tongue and floor of mouth, respectively, were cultured in Advanced DMEM supplemented with 1× Glutamax and 5% heat-inactivated FBS (GIBCO; Life Technologies; "complete" medium). All OSCC tumors from which the JSCC cell lines were derived represented primary resections and had therefore not been exposed to chemotherapy. For experiments to assess endogenous or growth factor stimulated effects, sera was omitted ("base" medium). Cell lines were authenticated via short tandem repeats profiling analyses at the Genetic Resources Core Facility (Johns Hopkins University, Baltimore, Md.).

Formalin fixed cells were characterized by incubation with (all antibodies from Abcam, Cambridge, Mass.) vimentin (1:200) or a pancytokeratin cocktail (AE1/AE3+5D3, 1:100) antibodies, followed by incubation with FITC or Texas Red conjugated secondary antibodies (Abeam) with 4',6'-Diaminidino-2-phenylindole dihydrochloride (DAPI) nuclear counterstaining. Images were obtained by using an Olympus BX51 microscope (Olympus, Japan), NikonDS-Fi1 digital camera (Nikon, Japan) and ImagePro 6.0 (Media-Cybernetics, Bethesda, Md.). Chemopreventives [4-HPR (Cedarburg Pharmaceuticals, Grafton, Wis.), 2-ME (Sigma-Aldrich, St. Louis, Mo.) and tocilizumab (Ohio State University James Cancer Hospital Pharmacy)] treatment doses were derived from concurrent cell proliferation (BrdU) and viability (WST) assays with optimal doses defined as retention of comparable cell viability as control cultures that suppressed proliferation. Double and triple agent treatments reduced proliferation to a greater extent than monotherapy, yet cell viabilities remained comparable (data not shown). The highly tumorigenic ATTC CRL-2095 human tongue OSCC cell line (2095sc), which has been well characterized [18, 25], was also evaluated and used for in vitro and in vivo studies.

Cell Line Matched OSCC Tumor, Peritumor Tissues and Normal Human Oral Mucosa pSTAT3 and pEGFR Characterization.

Formalin fixed (24-48 h) OSCC tumor tissues corresponding to central tumor, tumor free margins, and metastatic lymph nodes (for JSCC 1, 2 and 3), healthy oral mucosa and ulcerated, non-neoplastic oral mucosal tissues (obtained with Ohio State University IRB approval) were stained with hematoxylin and eosin in addition to signaling-relevant immunohistochemical stains: phospho-STAT3 rabbit monoclonal antibody (1:25, Cell Signaling Tec., Danvers, Mass.), phospho-EGF receptor rabbit monoclonal antibody (1:200, Cell Signaling Tec., Danvers, Mass.) or rabbit IgG isotype control (negative control) using standard preparation and incubation conditions, followed by biotinylated secondary antibodies incubation and Vectastain ABC reagent (Vector Laboratories, Burlingame, Calif.). IHC images were captured via an Olympus BX51 microscope (Olympus, Japan) and Nikon DS-Fi1 digital camera (Nikon, Japan).

Effect of Receptor Targeted Inhibitors on OSCC Signaling.

OSCC cell lines were pretreated for 1 hour with 0.01% DMSO (vehicle control), 100 nM afatinib (Selleckchem, Houston, Tex.) 100 nM Vargatef (Selleckchem), or 100 nM afatinib+100 nM Vargatef. Dosing levels were determined by concurrent proliferation and viability studies in conjunction with literature values [26]. The cells in every treatment group were then stimulated for 20 minutes with: vehicle (1 µl ddH$_2$O), 50 ng/ml EGF, 50 ng/ml VEGF, or 50 ng/ml EGF+50 ng/ml VEGF, followed by standard immunoblotting and data normalization relative to GAPDH. Additional experiments investigated the effects of 5 µM 4-HPR and 2.5 µM 2-ME treatment on phosphorylation and nuclear translocation of constitutively active STAT3 (JSCC1 and JSCC2) and stimulated (JSCC3) cell lines. Immunoblot images were captured (Li-Cor Odyssey imager) and analyzed (Li-Cor Image Studio, Version 4.0) to depict effects on treatment on phosphorylation relative to respective levels of GAPDH.

Determination of OSCC Cultured Cells' Endogenous Cytokine Secretion.

Conditioned media from 24-hour sera-deprived JSCC-1, JSCC-2 and JSCC3 cells were analyzed using the Proteome Profiler Human Cytokine XL Array (R&D Systems, Minneapolis, Minn.), with image capture and analyses via the Li-Cor Odyssey imager and Image Studio software (Li-Cor Biosciences, Lincoln, Nebr.). Sera-free conditioned media for IL-6, VEGF, TGF-α and EGF were analyzed by ELISAs (R&D Systems, Minneapolis, Minn.), with data expressed as pg/10$^6$ cells.

Molecular Modeling Studies to Assess 4-HPR-STAT3 and Related Kinases, c-Src and c-Abl Interactions.

Molecular modeling studies to evaluate 4-HPR's interactions and potential binding to STAT3's, c-Src's and c-Abl's associated tyrosine kinases and other sites were conducted using AutoDock Vina software [27] with protein structures obtained from the Protein databank [28]. STAT3, c-Src and c-Abl structures were optimized using Yasara and the default minimization algorithm. All ligands were constructed in Spartan 10 and minimized using Merck molecular force field. The optimized protein structures and ligands were docked using AutoDock Vina using an exhaustiveness of 100. Each calculation was repeated three times to ensure a thorough exploration of the binding site. Calculated binding free energies were used to determine a binding affinity (Ka) and dissociation constant (Kd) to compare to experimental data. $\Delta G=RT \ln(Ka)$ or $Ka=e^{-(\Delta G/RT)}$ and $Kd=1/Ka$. As c-Src can adopt one of two distinct conformations i.e. inactive (closed confirmation) and active (open), 4-HPR interactions were evaluated using both conformations. Similarly, c-Abl also has two formations i.e. inactive DFG-in and active DFG-out and both conformations were analyzed with the same common set of ligands at the ATP binding site.

4-HPR's Effects on Tumorsphere Formation and Retention of Proliferative Capacity.

$5 \times 10^5$ JSCC1 cells (tumorsphere-formation competent unlike JSCC2 and JSCC3 cells) were plated in complete medium with either vehicle control (0.01% DMSO) or 5 µM 4-HPR in Corning Ultra-Low attachment tissue culture flasks (Sigma-Aldrich, St. Louis, Mo.) Suspension cultures received fresh medium and treatment q d for 7 days, with daily images capture via the Nikon DS-Ri+NIS Element. After 7 days, cells and medium were harvested, centrifuged, and cells replated in standard culture flasks containing complete medium. Images were obtained daily and cells harvested after 7 days in culture. Cell number (hemocytometer counts) and viability (trypan blue exclusion) were obtained.

Single and Combined Treatment Effects on Signaling, Transcription Factor Activation and DNA Binding, and Cytokine Release.

Twenty four hour sera-deprived cells were treated for an additional 24 hours in sera free media with the following: 1) 0.01% DMSO (vehicle control), 2) 5 µM 4-HPR, 3) 2.5 µM 2-ME, 4) 1 µg/ml tocilizumab (TOC, ~2.55 µM) 5) 5 µM 4-HPR+2.5 µM 2-ME, 6) 5 µM 4-HPR+1 µg/ml TOC, 7) 2.5 µM 2-ME+1 µg/ml TOC, 8) 5 µM 4-HPR+2.5 µM 2-ME+1 µg/ml TOC. Following treatment, conditioned media were collected (ELISAs for IL-6, sIL-6R, TGF-α, VEGF, EGF, R&D Systems, Minneapolis, Minn.) and nuclear and cytosolic lysates (Nuclear Extract Kit, Active Motif, Carlsbad, Calif.) isolated for EMSAs (STAT3, NFκB p50 and p65, TransAM Transcription Factor ELISAs, Active Motif) and cytosolic and nuclear extracts for Westerns (NE-PER Nuclear and Cytoplasmic Extraction Reagents, ThermoFisher Scientific, Waltham Mass.). Western blot analyses used the following antibodies and dilutions: p-EGFR rabbit monoclonal antibody (1:1000 Cell Signaling Technologies), EGFR rabbit monoclonal antibody (1:2000 Cell Signaling Technologies), p-STAT3 rabbit monoclonal antibody (1:1000 Cell Signaling Technologies), STAT3 rabbit monoclonal antibody (1:2000 Cell Signaling Technologies), Erk1/2 mouse monoclonal antibody (1:2000, Cell Signaling Tec.), and phospho-Erk1/2 rabbit polyclonal antibody (1:1000, Cell Signaling Tec.), NF-κB p65 (rabbit monoclonal, 1:1000, Cell Signaling) and NF-κB p50 (rabbit 1:1000, Cell Signaling), β-actin mouse monoclonal antibody (1:10000 Santa Cruz Biotechnology), BCR-ABL (7C6, 1:1, 000, Thermo Fisher Scientific, Rockford, Ill.), GAPDH rabbit monoclonal antibody (1:10000 Cell Signaling Technologies), histone H3 and YY1 were used as the nuclear loading controls based on targeted protein molecular weight (Nuclear Loading Control and ChIP Grade monoclonal antibodies, Abcam, Cambridge Mass.). Densitometric analyses used Kodak 1D3 image analysis software, with data normalized to GAPDH (cytosolic) or histone H3 or YY1 (nuclear). For select experiments, cells were treated with the STAT3 inhibitor LY5 (0.5 µM) [29].

Formulation of Controlled-Release Polylactide-Co-Glycolide (PLGA) 4-HPR Implants for Xenograft Studies.

PLGA millicylinders, which consisted of 60% 50:50 acid end capped PLGA (24-38 kDa), were prepared by solvent extrusion method by dissolve 60% 50:50 acid encapped PLGA (24-38 kDa) in acetone, followed by addition of 4-HPR and excipients [MgCO3 and sodium deoxycholate (NaDC)], polymer drying and removal of the encasing silicon tubing. Optimization studies were conducted to enhance 4-HPR loading (up to 30%), release kinetics (20% NaDC), pore formation (MgCO3) and drug solubilization/prevention of crystallization (B-cyclodextrin, hydroxypropyl methyl cellulose (HPMC) K4M, and polyvinyl pyrollidone (PVP K30).

Determination of 4-HPR tumor levels entailed recording tumor wet mass, addition of internal standard (acitretin) and RIPA lysis buffer, followed by homogenization, addition of acetonitrile and centrifugation. Acetretin percent recovery was compared to a RIPA buffer/acetonitrile extraction control solution spiked with equivalent amount of acetretin and 4-HPR. Sera preparation entailed addition of acetretin and acetonitrile, sonication, followed by centrifugation. UPLC/UV analyses showed no evidence of the oxidized metabolite 4-oxo-4-HPR when compared to the calibration standard in either the tumor or sera samples.

Evaluation of Therapeutic Efficacy Using OSCC Tumor Xenografts.

SCC2095sc cells [$10^6$ cells suspended in 100 µl Matrigel (Corning Life Sciences, Corning, N.Y.)] were subcutaneously injected in the flanks of 6 week old male nude mice (n=6 per treatment group). Tumor measurements were recorded daily with calipers (greatest length and greatest width) and final tumor volumes calculated via tumor volume V=(length×width)×½. Treatment groups consisted of: 1) control (PBS injections)+blank (no drug) PLGA implants, 2) 2-ME (1 µg/100 µl PBS, b.i.d.)+blank PLGA implant, 3) 4-HPR releasing PLGA implant+PBS injections, 4) TOC q.d. (0.3 µg/100 µl PBS)+PLGA blank implant, 5) 2-ME (1 µg/100 µl PBS, b.i.d.)+4-HPR releasing PLGA implant, 6) 2-ME (1 µg/100 µl PBS, b.i.d.)+TOC q.d. (0.3 µg/100 µl PBS)+blank PLGA implant, 7) TOC q.d. (0.3 µg/100 µl PBS)+4-HPR releasing PLGA implant, 8) 2-ME (1 µg/100 µl PBS, b.i.d.)+TOC q.d. (0.3 µg/100 µl PBS)+4-HPR releasing PLGA implant. By day 14 post injection, all mice had measurable tumors and treatment began on day 15. Attempts to achieve uniform tumor size distribution among groups by animal transfer resulted in aggression toward the new cage mates. Pretreatment mean tumor volumes therefore varied among treatment groups. PLGA implants (via trocar) and injections were placed in the center of the tumor. At day 28 post OSCC xenograft placement final tumor measurements were obtained, the mice were euthanized and OSCC tumors along with lung, liver and sera were harvested for pharmacokinetic, histologic and IHC analyses (Ki-67, cleaved caspase-3 and involucrin). Image analyses of the nuclear stains (Ki-67 and cleaved caspase 3) were conducted using Image-Pro Plus 6.2 software (Media Cybernetics, Rockville, Md.).

Statistical Analyses:

Data normality (Shapiro Wilks normality test) determined whether parametric or nonparametric analyses were employed. The Wilcoxon matched pairs signed rank test was used to assess the effects of 4-HPR treatment on STAT3 activation. Effects of combination treatments on STAT3-DNA binding and cytokine release as well as image analyzed IHC tumor data were evaluated by the Kruskal Wallis ANOVA followed by the Dunn's Multiple Comparison post-hoc test (individual cell lines, IHC data) or One Way ANOVA, followed by Tukey's multiple comparison test (combined cell line data). A paired t test (pre versus post treatment individual tumor measurement) was used to assess the effects of treatment on tumor volume.

Results

JSCC Cells Retain Features of Their Corresponding Tumor Tissues.

All JSCC lines contained dual cytokeratin and vimentin staining cells. Normal oral epithelia showed sparse pSTAT3 and no pEGFR nuclear staining in basal cells with modest increases noted following ulceration. Cell-matched tumor tissues, however, showed membrane-associated pEGFR with highest expression in the JSCC2 tumor tissue. pSTAT3 nuclear staining was highest in the JSCC1 and JSCC2 tumors; similar to corresponding cells lines' constitutive STAT3 phosphorylation. All three JSCC lines also demonstrated constitutive EGFR and/or STAT3 signaling similar to their corresponding tumors' high in vivo expression.

Afatinib and Vargatef's Effects are Cell Line Specific.

Figure 1B:
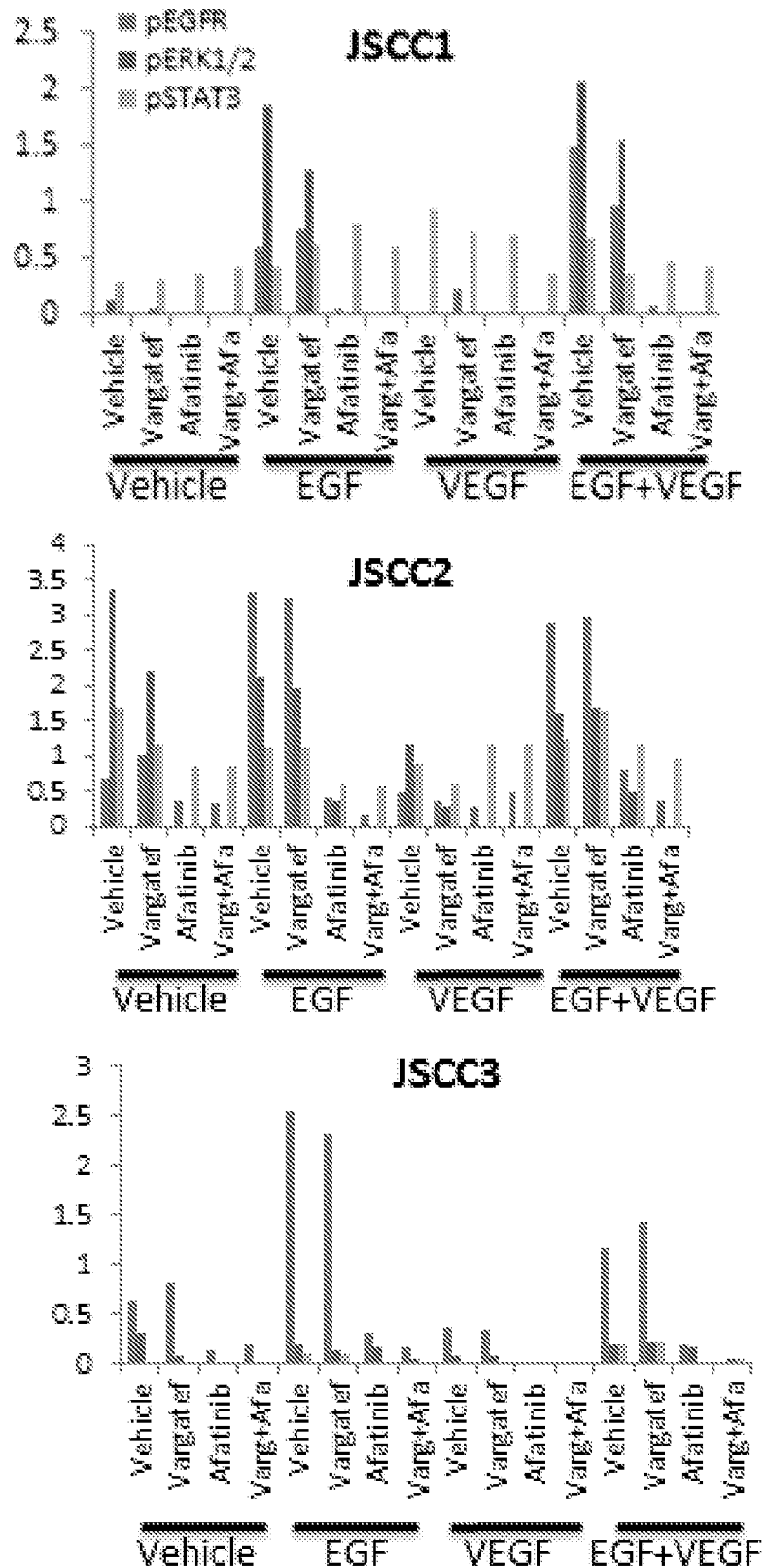

JSCC2 cells demonstrated high constitutive activation of pSTAT3 and pERK1/2 and modest levels of pEGFR. The other lines showed modest (JSCC3-pEGFR and ERK1/2) and modest (JSCC1-pSTAT3) constitutive activation, respectively. EGF stimulation increased phosphorylation of EGFR (all lines) and ERK1/2 phosphorylation (JSCC1 and 2) whereas VEGF elicited more modest responses in the JSCC1 and 2 lines, primarily increasing pSTAT3 levels (FIGS. 1A and 1B). Responses to the EGFR tyrosine kinase inhibitor (Afatinib) and the triple angiogenic (VEGF, bFGF, PDGF) tyrosine kinase inhibitor (Vargatef) were also cell-line dependent. Although Afatinib and Vargatef treatment reduced phosphorylation in JSCC3 cells at the EGFR, ERK1/2, and STAT3 levels, high to moderate levels of phosphorylated STAT3 persisted in JSCC1 and JSCC2 cells despite treatment(s).

Cell Lines Release Unique Cytokine Profiles.

Figure 1C:
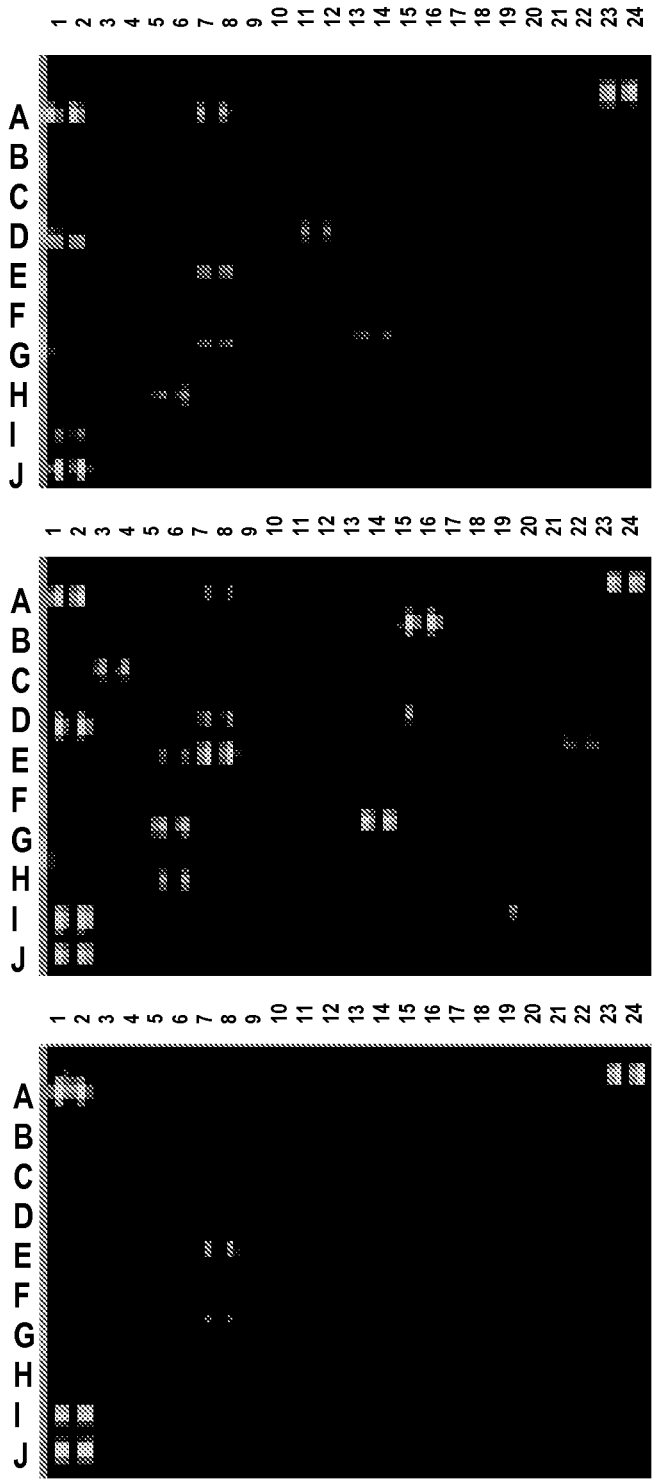

Proteome profiling showed JSCC2 cells released the most cytokines (19) relative to 9 and 6 for the JSCC1 and JSCC3 cells respectively (FIGS. 1C and 1D). All three cell lines released Dickkopf-1, Interleukin-8, and Macrophage migration inhibitory factor. The constitutive pSTAT3 and tyrosine kinase blockade resistant JSCC1 and JSCC2 cells exclusively released Angiogenin, CXCL1 and PDGF-AA. Quantification of the STAT3 activating cytokines (IL-6, EGF, and TGF-α) by ELISAs revealed high levels of IL-6 release in JSCC2 and the highly tumorigenic 2095sc cells, followed by moderate and negligible IL-6 release in JSCC1 and JSCC3 cells respectively (FIG. 1E). None of the cell lines released EGF or TGF-α. 4-HPR inclusion (5 µM, fresh treatment q.d., base medium) increased IL-6 release, which was greatest at the 48 h time point with increases of ~50% and ~20% in the JSCC1 and JSCC2 cells respectively (data not shown).

4-HPR (5 µM) Singularly and in Combination with 2-ME (2.5 µM) and TOC (1 ug/ml) Inhibits STAT3 Cytosolic Phosphorylation and Nuclear Translocation.

Figure 2A:
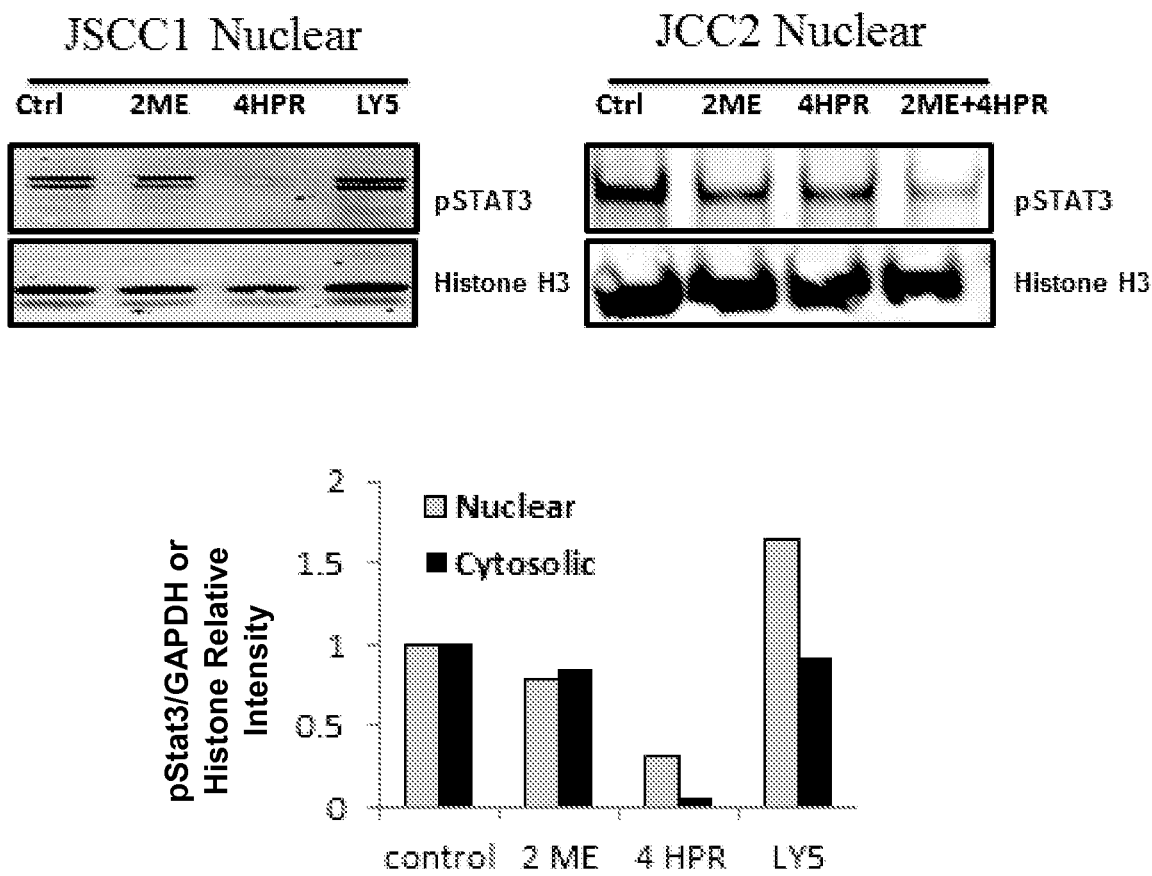
FIGS. 2A, 2B, and 2C show the treatment effects of fenretinide (4-HPR, 5 µM), 2-methoxyestradiol (2-ME, 2.5 µM) and the STAT3 inhibitor LY5 (0.5 µM) on STAT3 phosphorylation and nuclear translocation. (A) (JSCC1 cells) (B) (JSCC2 cells) and (C) (JSCC3 cells) were evaluated. Cytosolic and nuclear proteins were harvested from sera deprived JSCC1 and JSCC2 cell lines following 24 h of treatment (5 µM 4-HPR, 2.5 µM 2-ME, or 0.5 µM LY5) or vehicle (0.1% DMSO) control. Multiple experiments confirmed 5 µM 4-HPR treatment significantly reduced constitutive STAT3 phosphorylation and pSTAT3 nuclear translocation in the STAT3 constitutively active JSCC1 and JSCC2 cells (p<0.05, Wilcoxon matched pairs signed rank test, n=7). As the JSCC3 cells don't constitutively express pSTAT3, these cells underwent 24 h stimulation in base medium supplemented with 10 ng/mL of IL-6 or 5 ng/mL of TGF-α, with or without 4-HPE, 2-ME or LY5 treatment, followed by harvest. The combination treatment of 2ME and 4-HPR significantly inhibited IL-6 or TGF-α induced pSTAT3 nuclear translocation in JSCC3 cells. (n=3, p<0.05, Wilcoxon matched pairs signed rank test).
Figure 2B:
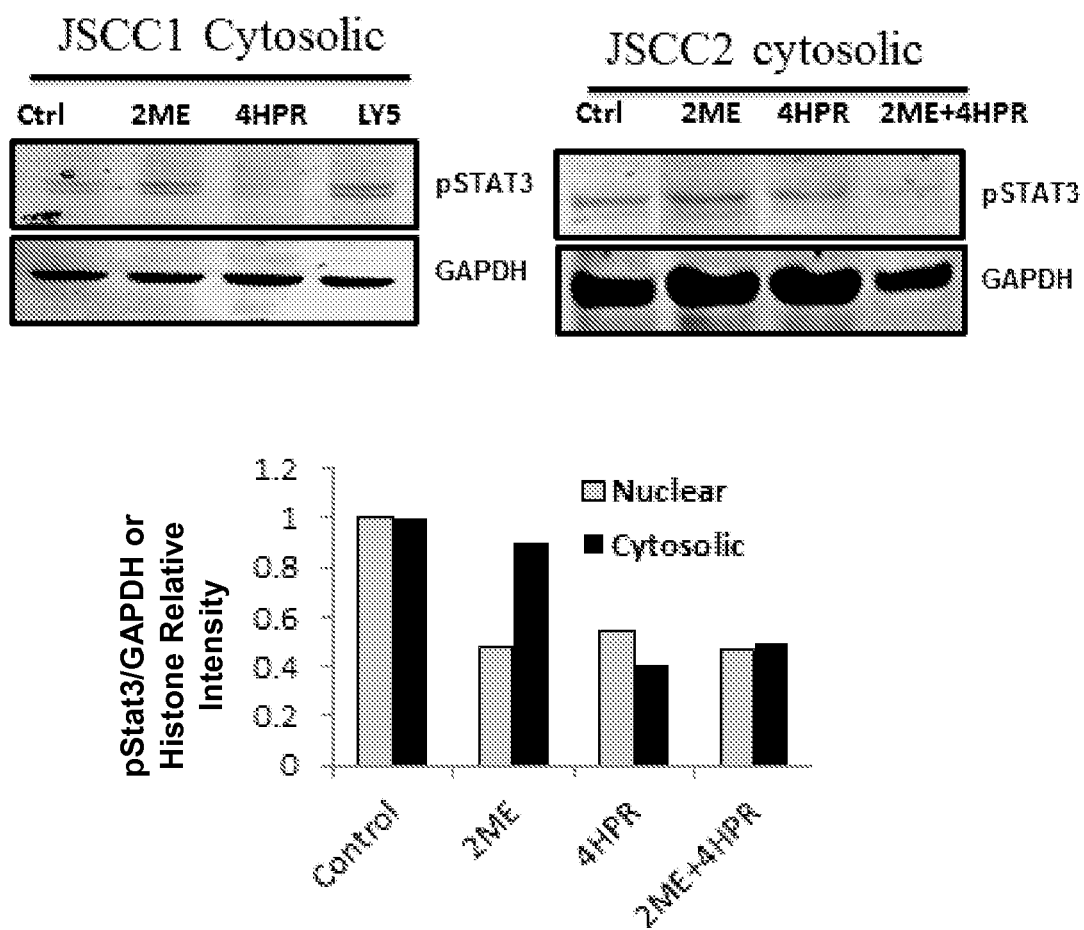

Cytosolic and nuclear extract immunoblots demonstrated that 5 µM 4-HPR suppressed STAT3 phosphorylation and nuclear translocation in the STAT3 constitutively phosphorylated cell lines (FIG. 2A). Also, 4-HPR was appreciably more effectively at suppressing STAT3 activation and nuclear translocation in JSCC1 cells relative to the STAT3 inhibitor LY5 [29].

Figure 2C:
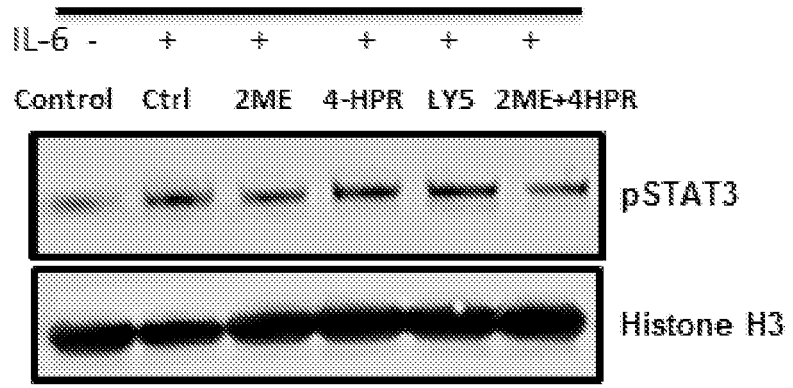
Figure 2C:
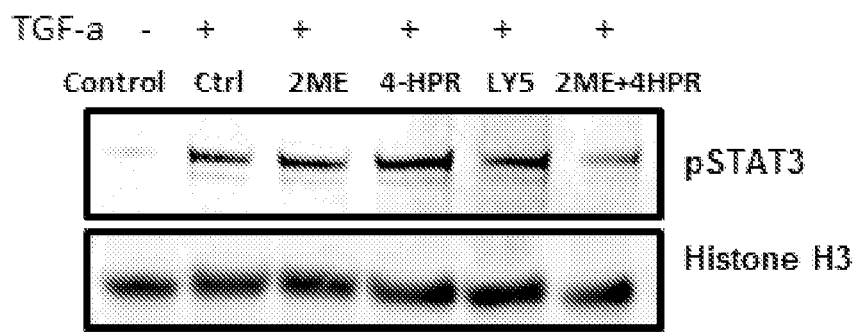
Figure 2C:
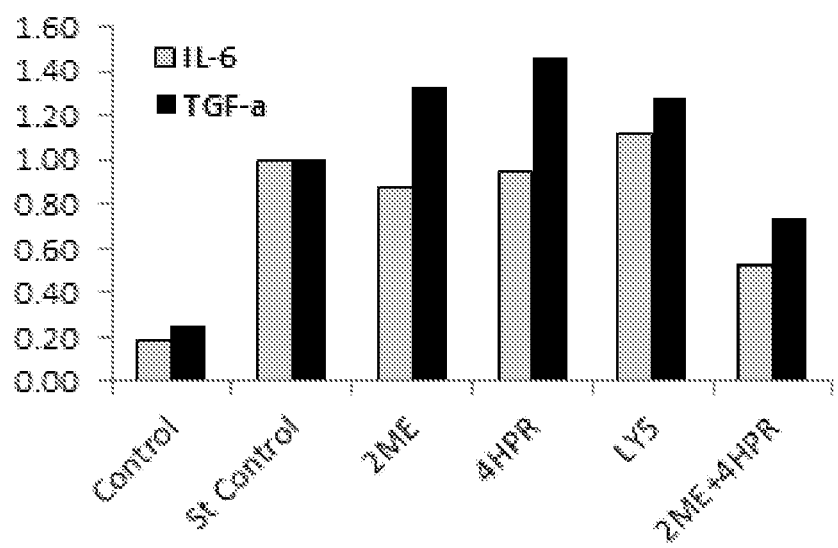

Selected combination treatments induced reduction of STAT3 and pSTAT3 levels in 2095sc cells and to a lesser extent the JSCC1 and 2 lines. In addition the treatment combinations of TOC+4-HPR and TOC+4-HPR+2-ME significantly inhibited STAT3 phosphorylation [p<0.05, n=12 total with n=3 for every individual cell line (FIG. 2C, including JSCC3)], Kruskal Wallis followed by Dunn's Multiple Comparison post hoc test).

Molecular Modeling of 4-HPR Interactions with STAT3 and Additional Nonreceptor Kinases c-Abl and c-Src.

Figure 3A:
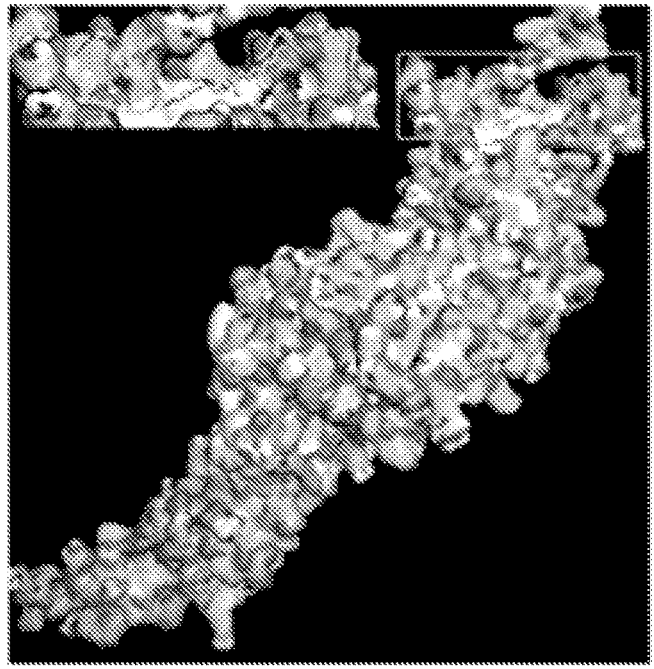
FIG. 3A shows that 4-HPR demonstrates both moderate and high-affinity binding at STAT3's SH2 dimerization site. The STAT3 protein structure was obtained from the Protein databank 1BG1. The STAT3 structure was optimized via Yasara et al. using the default minimization algorithm. All ligands were constructed in Spartan $10^2$ and minimized using MMFF. The optimized protein structure and ligands were docked using AutoDock Vina employing an exhaustiveness of 100. Each calculation was repeated three times to ensure a thorough exploration of the binding site. Previous results have shown that flexible amino acid side chains provide for better results[6] therefore the side chains for amino acids: 591, 592, 595, 597, 609, 611-613, 620, 623, 635, 637, 638, 640, 657, 705-710 and 712 were made flexible to ensure a more realistic binding mode for all calculations. The binding energy (−14.2) observed for 4-HPR at the newer binding site imply nM levels of 4-HPR would impede STAT3 dimerization.

Molecular modeling data revealed that 4-HPR and its oxidized metabolite 4-oxo-4HPR bind along the arm (right side of the figure above with the amino acid side chains displayed), while other STAT3 inhibitors bind in the small pocket with the beta-sheet near Tyr 640 and Lys 591 (lower left side of the amino acids with side chains showing, consistent with models for XZH-5, STA-21, pCinn-Nle-mPro-Gln-NHBn, LYS5 and others. (FIG. 3A). Notably, 4-HPR also binds with extremely strong affinity (−14.2 kcal/mol) at an additional binding site in the SH2 domain. At this energy level, 4-HPR should demonstrate efficacy at nanomolar levels, interfere with STAT3 dimerization and due to Tyr705's proximity to SH2, possibly perturb phosphorylation.

Figure 3B:
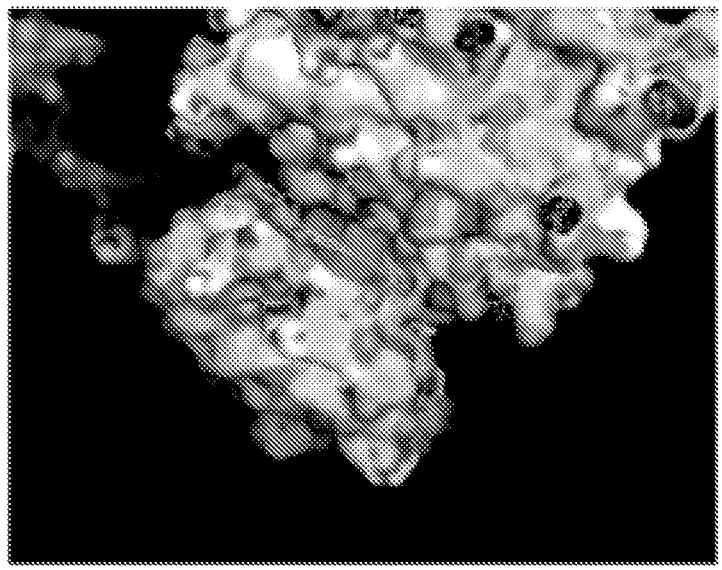
FIG. 3B shows that kinase inhibitor site molecular docking data suggest 4-HPR has nanomolar level affinity for c-Src's ATP binding site. With the exception of 4HPR and KX2-391 all other evaluated ligands bind in an analogous fashion to ATP i.e. lying in a "groove" on the protein surface between a beta-sheet and random coil. In contrast, 4HPR and KX2-391 bind with an orientation more perpendicular to the protein surface (in the same groove) and penetrate much deeper into c-Src's interior. This unique binding conformation is only 0.5 kcal/mol lower in binding energy compared to parallel to the groove. Finally, as c-Src is self-inhibited in the closed confirmation, binding and affinity data reflect modeling data employing c-Src's active "open" confirmation.

4-HPR and 4-oxo-4HPR also demonstrated nanomolar level binding affinities (−10.6 kcal/mol for both) for c-Src's ATP binding site in both the active (FIG. 3B) and inactive configurations. These affinities are comparable to the c-Src selective inhibitors Dastinib, AP23464 and PD173955. With the exception of 4-HPR and KX2-391, all other c-Src inhibitors bind similarly i.e. the inhibitor lies in a "groove" on the protein surface between a beta-sheet and random coil. In contrast, 4-HPR and KX2-391 bind with a more perpendicular orientation relative to the protein surface yet within the same groove as the other inhibitors (FIG. 3B). 4-HPR's unique binding orientation enables deeper penetration into c-Src's protein interior.

Figure 3C:
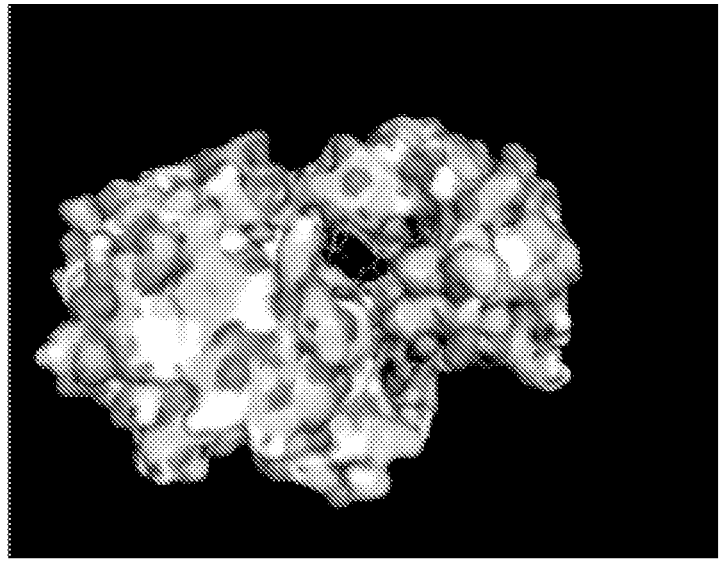
FIG. 3C shows that 4-HPR also demonstrates nanomolar level affinity for c-Abl's kinase ATP binding site. As Abl also has active "open" and inactive "closed" conformations, modeling data depict interactions with the open conformation. Notably, the fusion of BCR sequences to ABL during the translocation associated with CML ("Philadelphia Chromosome"), increases the tyrosine kinase activity of c-Abl.

Similarly, 4-HPR and 4-oxo-4-HPR are also nanomolar level inhibitors of c-Abl's ATP binding site in both its active and inactive conformations (binding energies of −12.2 and −13.1 kcal/mol, respectively) (FIG. 3C). Although 4-HPR and 4-oxo-4HPR bind in the same pocket as other inhibitors, 4-HPR and to a lesser extent 4-oxo-4HPR bind in an orientation that places them deeper into c-Abl interior analogous to bosutinib, dastinib and KX2-391 (FIG. 3C). Notably, 4-HPR binds with appreciably higher affinity at the ATP binding sites relative to ATP (10 and 100 fold higher for c-Src active and inactive sites and 1000 fold greater for c-Abl active and inactive sites.

4-HPR Inhibits Tumorsphere Formation and Eliminates Further Growth.

Figure 4A:
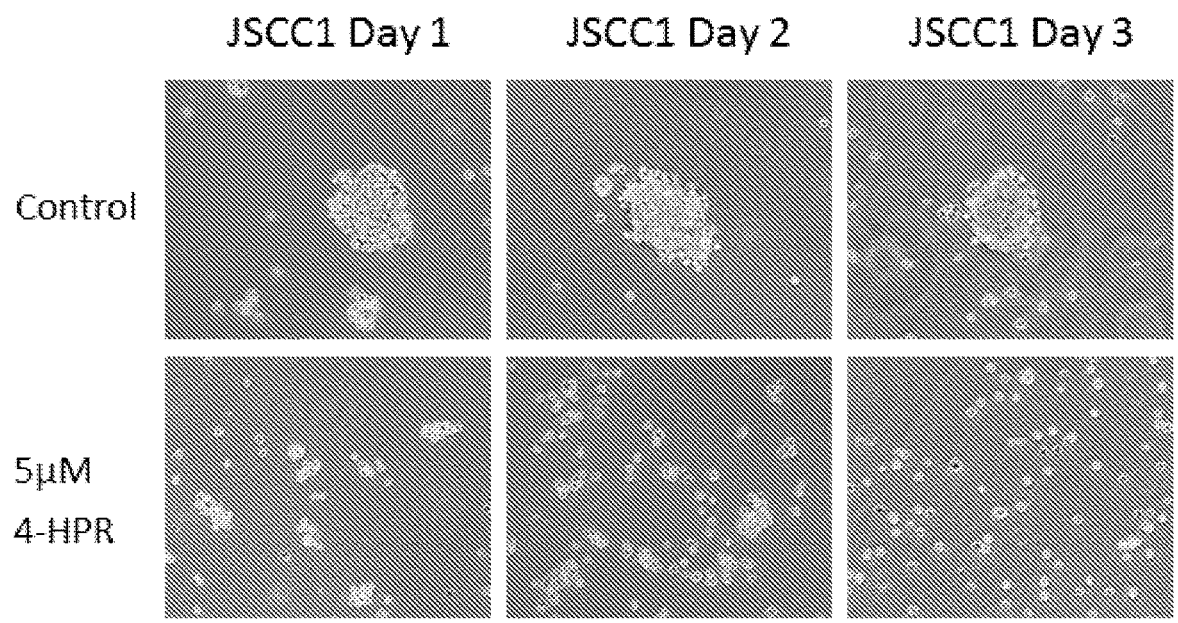
FIG. 4A shows that 4-HPR inhibits tumorsphere formation. JSCC1 cells were seeded at density of 5×$10^5$ cells in Advanced DMEM+5% FBS+1× GlutaMAX Supplement in Ultra-Low Attachment surface T-25 flasks with DMSO control (0.05%) and 5 µM 4-HPR treatment. Cell suspension cultures were treated for 3 days with fresh treatment every 24 h. While control cultures formed tumorspheres by 24 h, 4-HPR treated cellular interactions were limited to small cell aggregates. (Image scale at 100×.)
Figure 4B:
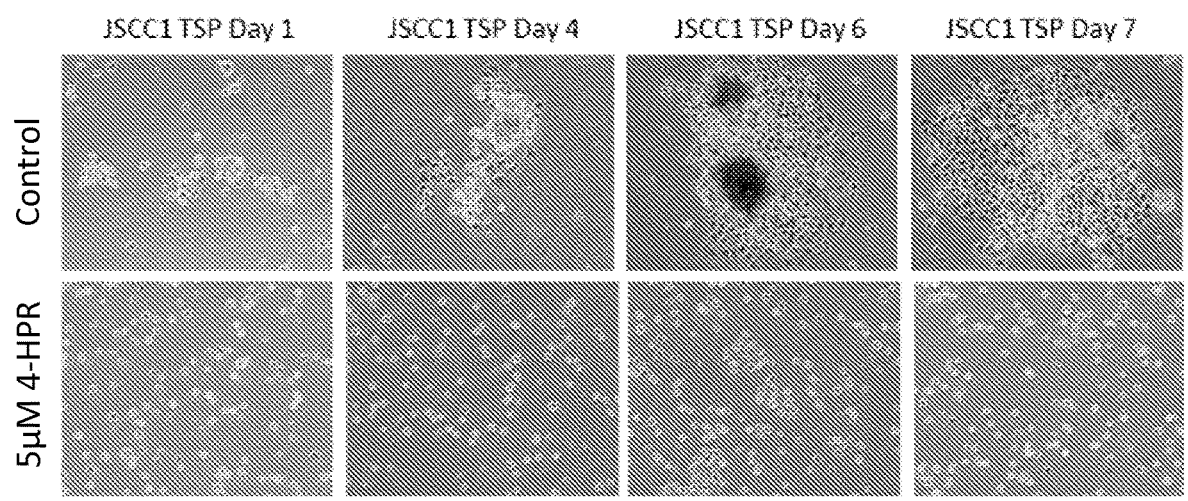
FIG. 4B shows that cell attachment inhibition remains following 4-HPR removal. Following the treatment described in FIG. 4A above, the JSCC1 control and 4-HPR treated cells were returned to standard tissue culture flasks for seven days in 4-HPR free complete medium (Advanced DMEM+5% FBS+1× GlutaMAX Supplement). The control cultures readily reattached, formed cellular islands with readily apparent mitotic figures and possessed high viabilities (>95%, trypan blue exclusion). In contrast, the cells previously treated with 4-HPR failed to reattach and were uniformly non-vital. (Image scale 100×.)

While $5 \times 10^5$ JSCC1 cells (and not JSCC2 or 3 cells) readily formed tumorspheres in low attachment flasks+ complete medium, 5 µM 4-HPR inclusion inhibited tumorsphere formation (FIG. 4A) Following re-plating in complete medium in standard tissue culture flasks, control cells reattached, resumed proliferation and retained ≥95% viability after 7 days in culture. In contrast, 5 µM 4-HPR treated cells were not viable 100% trypan blue uptake) and failed to reattach. (FIG. 4B).

Combination Chemopreventive Treatments Inhibit STAT3-DNA Binding.

Figure 5A:
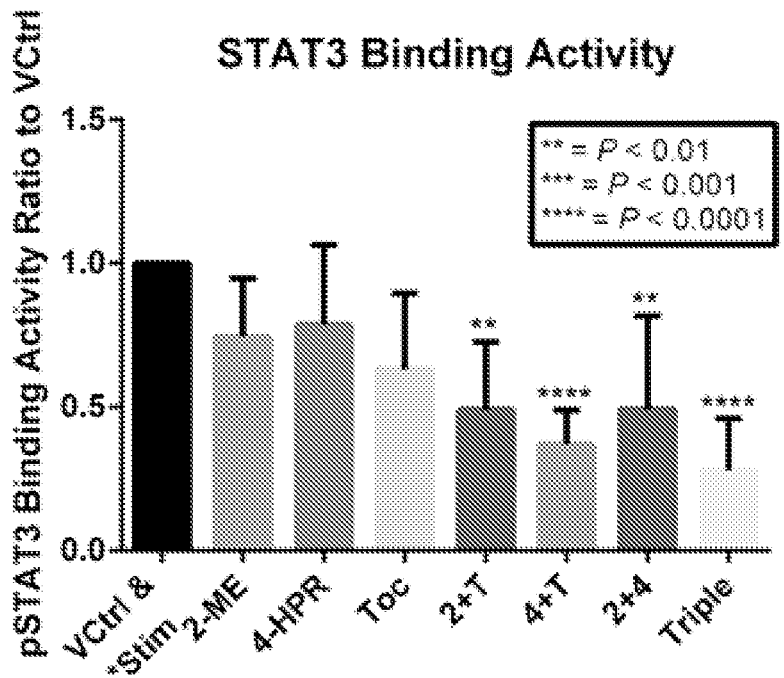
FIGS. 5A and 5B show the evaluation of the effects of single and combination treatment of fenretinide (4-HPR, 5 μM), 2-methoxyestradiol (2-ME, 2.5 μM) and the IL-6R inhibitor TOC (1 ug/ml) on STAT3-DNA binding and on release of the stromal and tumor cell activating, trans-signaling molecule, sIL-6R. (A) Treatment effects of STAT3-DNA binding. All cell lines with constitutive pSTAT3 expression (2095sc, JSCC1, JSCC2) were sera deprived for 24 h, followed by an additional 24 hours of treatment in sera-free medium that contained: control (0.1% DMSO), 5 μM 4-HPR, 2.5 μM 2-ME, 1 μg/ml TOC (initial agent concentrations same for single and combinations). As the JSCC3 cells don't constitutively express pSTAT3, these cells underwent 24 h stimulation in base medium supplemented with 10 ng/mL of IL-6 and 5 ng/mL of TGF-α, with or without 4-HPR, 2-ME and TOC followed by harvest. Collective cell line data (expressed as change relative to cell-line matched control) revealed dual and triple chemo-preventive combinations significantly reduced STAT3 binding with its cognate DNA binding sites. (n=13, Kruskal Wallis ANOVA followed by Dunn's Multiple Comparison post hoc test). Corresponding analyses of single cell line data (n=3 for all cell lines with exception of n=4 for JSCC2) revealed triple treatment significantly ($p<0.05$) inhibited STAT3 binding in every individual cell line with constitutively active STAT3 (JSCC1, JSCC2 and SCC2095sc). (B) Effects of treatment on cell line release of sIL-6R. All four cell lines released sIL-6R [levels ranges from ~750 fg/$10^6$ (JSCC2 cells baseline) to ~3,000 fg/$10^6$ cells (stimulated JSCC3 cells, baseline production JSCC3~2,000 fg/$10^6$ cells). The sIL-6R humanized monoclonal antibody (tocilizumab) when administered singularly and in a triple treatment combination significantly inhibited sIL-6 release ($p<0.005$, Kruskal Wallis followed by Dunns Multiple Comparison test).

While monotherapy did not significantly inhibit STAT3-DNA binding, combination treatments that included 4-HPR [(4-HPR+2-ME, p<0.05), (4-HPR+TOC, p<0.01)] and all three agents (4-HPR+2-ME+tocilizumab, p<0.001) significantly inhibited STAT3-DNA binding (FIG. 5A).

Figure 5B:
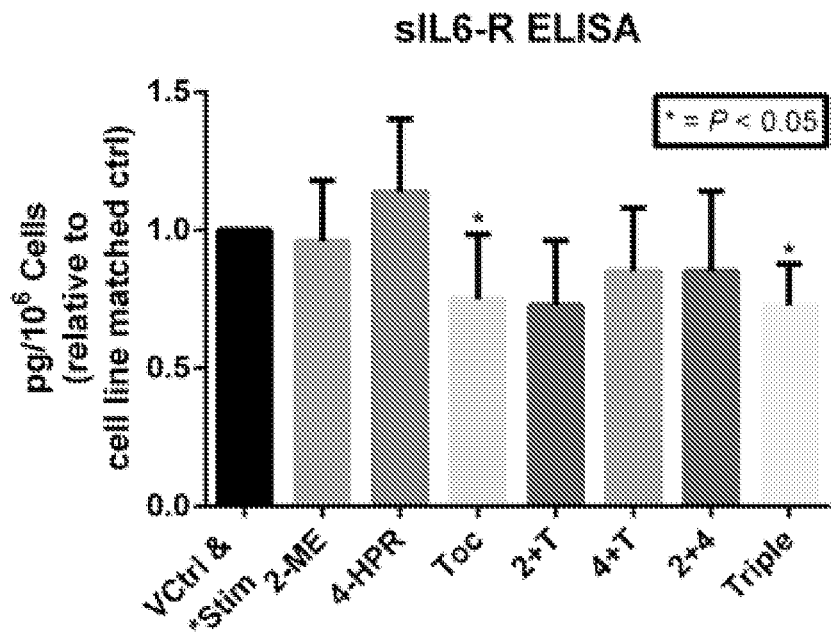

All cell lines produced sIL-6R. JSCC3 cells' sIL-6R levels were the highest (albeit post 10 ng/mL of IL-6 and 5 ng/mL of TGF-α stimulation as opposed to other sera deprived lines), followed by constitutive production in the 2095sc, JSCC1 and JSCC2 cells respectively. Two treatments i.e. TOC and the 4-HPR, 2-ME and TOC triple treatment significantly reduced sIL-6R release (FIG. 5B).

Studies to assess effects of treatment on binding of the NF-κB subunits p65 and p50 showed modest reduction only in the 2095sc (p65) and JSCC2 (both) cell lines.

In Vivo Studies Show Benefits of Tumor-Directed, Multimodal Therapy.

All mice injected with Matrigel-2095sc cells developed OSCC tumors. Although all OSCC xenografts were well-vascularized, necrotic foci were observed in regions with high proliferation indices and adjacent to 4-HPR implants. Lymphovascular (several mice) and perineural (single mouse) invasion by tumor cells were observed in the 2-ME treatment group; the mouse with perineural invasion had lung metastases at sacrifice. Pretreatment tumor volumes varied appreciably within and among treatment groups (FIG. 6), findings that may reflect variations in tumor growth capacity including angiogenesis. Only the TOC, TOC+4-HPR implant, and TOC+2-ME+4-HPR implant treatments prevented a significant increase in tumor volume over 14 days (See FIG. 6A). Notably, the TOC+2-ME+4-HPR implant group's mean pretreatment tumor volumes were nearly two fold higher than TOC group. The mean tumor fold size increases for the TOC and TOC+2-ME+4-HPR treatments were 2.13 and 1.72, respectively. 4-HPR implants released between 300-370 µg drug and achieved tissue levels of 331+/−134 µM. IHC image analysis of the OSCC tumors' Ki-67 staining revealed that while all treatments decreased OSCC cell proliferation relative to control tumors, significant suppression was only observed in selected groups [2ME+TOC+4-HPR, TOC+4-HPR, 2-ME+TOC p≤0.001; 2-ME+4-HPR p≤0.05] (FIG. 6). Finally, although treatments occurred just below the skin, no disruption, ulceration or histologic changes were observed in the overlying epidermis. Ki-67 staining was apparent in the basal layer keratinocytes consistent with normal proliferation. UPLC/UV analyses showed no evidence of the oxidized metabolite 4-oxo-4-HPR when compared to the calibration standard in either the tumor or sera samples. Furthermore, 4-HPR sera levels were below LLOQ (<50 ng/ml) in all mice that received PLGA implants.

Discussion

This example evaluated multifaceted chemopreventives' abilities to suppress OSCC tumor-promoting pathways i.e. gratuitous signaling, constitutive transcription factor activation and DNA binding, anchorage independent growth and tumorigenesis [21-25]. Collectively, these results show combinations of agents with complementary mechanisms of action provided enhanced efficacy at both the in vitro and in vivo levels.

Afatinib and Vargatef signaling inhibition was cell-line dependent and negatively correlated with constitutive ERK1/2 and STAT3 signaling. There were also marked inter-line differences in both the numbers and levels of cytokines produced. Consistent with the STAT3-IL-6 feed forward loop, lines with constitutive STAT3 activation released higher IL-6 levels. IL-6 levels detected (range ~100-1,600 pg/$10^6$ cells) were comparable to IL-6 release from other human cancer cells (ovarian 100-200 pg/$10^6$ cells, prostate 850-1250 pg/$10^6$ cells) [32, 33]. Similarly, VEGF release (range ~1,000-3,000 pg/$10^6$ cells) also compared favorably to previous OSCC cell data (1,500 pg/$10^6$ cells) [34]. Consistent with the presence of the tumor promoting Bcr-Abl oncogene, the 2095sc cells released the highest levels of IL-6 and VEGF among the OSCC cell lines.

Molecular modeling studies showed concordance between 4-HPR binding and other STAT3 inhibitors i.e. fairly weak binding ($IC_{50}$ values in the µM range) at the "standard" SH2 STAT3 binding site. 4-HPR, however, also binds to a novel STAT3 SH2 site at a high affinity that conveys a nanomolar energy equivalency level. In addition, 4-HPR's binding orientation enables greater penetration relative to standard inhibitors into Src's and Abl's protein interiors at their ATP binding sites. This unique orientation results in nanomolar level affinities that are 10 fold (Src) and 100 fold (Abl) greater than the binding of the endogenous ligand, ATP. Notably, both Src and Abl kinases contribute to constitutive STAT3 activation [35] and Abl functions in cell transformation via a Src/Abl/Rac/JNK/STAT3 signaling cascade [36]. Thus, 4-HPR's enhanced STAT3 inhibition relative to standard inhibitors e.g. LY5 [29] likely reflects both its unique high affinity SH2 interaction plus its upstream Src and Abl inhibition. Although Bcr-Abl is generally associated with chronic myelogenous leukemia, two OSCC clinical trials evaluated systemically administered Bcr-Abl inhibitors [Saractinib (dual Src and Bcr-Abl inhibitor) and Dasatinib (multikinase inhibitor of PDGFR, Bcr-Abl, c-Kit)] in recurrent or metastatic OSCC patients [37, 38]. While unsuccessful, these studies confirmed a Bcr-Abl association with OSCC pathogenesis [37, 38]. As the Abl ATP binding site remains constant in the Bcr-Abl fusion protein [31], 4-HPR's ATP-blocking effects should extend to this oncoprotein. This current example depict 4-HPR's capacity to perturb tyrosine kinases via binding at higher affinities than the natural ligand at functional sites. Although chemically derived from retinol i.e. retention of the trimethylcyclohexenyl group and polyene chain, 4-HPR replaces retinol's hydroxyl group with a stability enhancing amide and a redox-active phenol ring. These changes apparently provide 4-HPR with unique protein interactive and binding capacities. Structure function analyses to assess 4-HPR-retinol binding protein interactions suggested bound 4-HPR induced both steric hindrance and target protein conformational changes [39]. Current and previous modeling-functional analyses [21] show 4-HPR's high affinity protein interactions extend to tyrosine kinases integral for carcinogenesis.

While 4-HPR suppressed STAT3 phosphorylation and nuclear translocation in a cell line dependent fashion, combining 4-HPR with TOC and 2-ME provided the most pervasive effects. Furthermore, 4-HPR, 2-ME and/or TOC combination treatments significantly inhibited pSTAT3 binding to its cognate DNA site. Numerous mechanisms may be attributable for these results including 4-HPR's inhibition of STAT3 phosphorylation, impaired nuclear translocation potentially attributable to 4-HPR-mediated steric hindrance, intranuclear dephosphorylation, and/or upregulation of SOCS-1 [40]. Of interest, unphosphorylated STAT3 can bind with unphosphorylated NF-κB resulting in complex-mediated activation of κB-dependent genes including IL-6, VEGF, COX-2 [41]. Studies to assess 4-HPR, 2-ME and TOC's effects on two primary NF-κB subunits (p50 and p65) at κB DNA binding sites revealed 4-HPR+TOC reduced DNA binding of the gene activating p65 subunit in the two high VEGF producing cell lines while binding of the apoptosis-associated p50 remained constant in the 2095sc line [42]. While previous studies demonstrated 2-ME disrupted NF-κB activation and DNA binding in neuroectodermal brain tumors [43], the data in this example, which showed 2-ME didn't inhibit OSCC cells' NF-κB activation (data not shown), imply tumor type specificity. As STAT3 retains p65 in the nucleus [13], this data may also reflect reduced nuclear STAT3 levels. Also, these results showed, for the first time, sIL-6R production by OSCC cells. Although OSCC sIL-6R levels released by $10^6$ OSCC cells were negligible, the number of cells in an OSCC tumor could elevate production to tumor-enabling levels. As s-IL6R enables IL-6 signaling in cells without IL-6R, serves as an IL-6 carrier and extends IL-6 half-life, autologous OSCC sIL-6R release would enhance tumorigenesis. Not surprisingly, treatments that disrupted intracellular signaling concurrently inhibited sIL-6R release. These data show local implant-induced sIL-6R inhibition could also perturb sIL-6R release from high output cells like PMNs which would significantly impact the tumor milieu [44]. In addition, 4-HPR inclusion induced anoikis in otherwise tumorsphere-competent cells. These findings are consistent with STAT3's role in anoikis resistance, STAT3's and FAK's contributions to anchorage independent growth, and 4-HPR's interference with FAK and STAT3 function [21, 45, 46]. As tumorsphere formation is associated with adoption of cancer stem cell features including self-renewal and resistance to cytotoxic agents, 4-HPR's prevention of anchorage independent growth could be highly beneficial for chemoprevention.

Although the long range goal is to develop an effective locally delivered secondary OSCC chemopreventive strategy, in vivo studies assessed capacity to suppress growth in established OSCC tumors. The rationale for selection of this in vivo model is as follows. As the OIN to OSCC transition can be extremely brief at former resection sites, formation of microtumor foci is a realistic clinical concern [2, 3]. Provided this scenario, secondary chemopreventives would be required to inhibit OSCC tumor development, albeit on a smaller scale than currently tested. From the experimental perspective, a tumor initiation xenograft model optimally includes a cell line that generates uniformly-sized OSCC tumors in 100% of injected mice. Because such a line was not yet established in the lab, a model was employed with a higher level of experimental control i.e. confirmation of tumor growth was confirmed prior to treatment and integration of pretreatment and posttreatment tumor size comparisons. Notably, the most aggressive OSCC cell line, characterized by high production of OSCC-relevant cytokines i.e. IL-6, VEGF and sIL-6R and presence of the Bcr-Abl oncoprotein was selected for implantation.

Previous studies demonstrated 2-ME liposomes (150 mg/kg, i.p.) significantly reduced HNSCC tumor formation and 2-ME+paclitaxel (20 mg/kg i.p.) suppressed growth of established tumors [47]. The lack of 2-ME efficacy to reduce tumor size in these studies likely reflects both drug instability (~4 h half-life) and use of appreciably (>2,000) lower doses. Additionally, tocilizumab (100 µg i.p.) significantly reduced HNSCC tumor initiation in scid mice; however this treatment didn't significantly inhibit established tumor growth [48]. In contrast, the data showed appreciably lower local tocilizumab doses (0.3 µg q.d.) significantly inhibited OSCC tumor growth. Further, as systemic tocilizumab can cause significant immune suppression, local delivery is preferable from both efficacy and safety perspectives. Despite achieving tumor 4-HPR levels that were appreciably greater than apoptosis-inducing 10 µM [21], 4-HPR implants only significantly inhibited tumor growth when used with other agents. These data show that released 4-HPR was largely inaccessible to the tumors, potentially due to high affinity binding to centrally located residual Matrigel and extravasted erythrocytes. Previous results from pilot studies, which entailed placement of two 4-HPR releasing implants adjacent to OSCC tumors, demonstrated significant tumor inhibition and emphasize the importance of both implant location and number. Finally, the absence of any detectable levels of 4-HPR or its metabolites in the sera of any animals emphasizes the safety of PLGA local drug delivery.

Figure 6A:
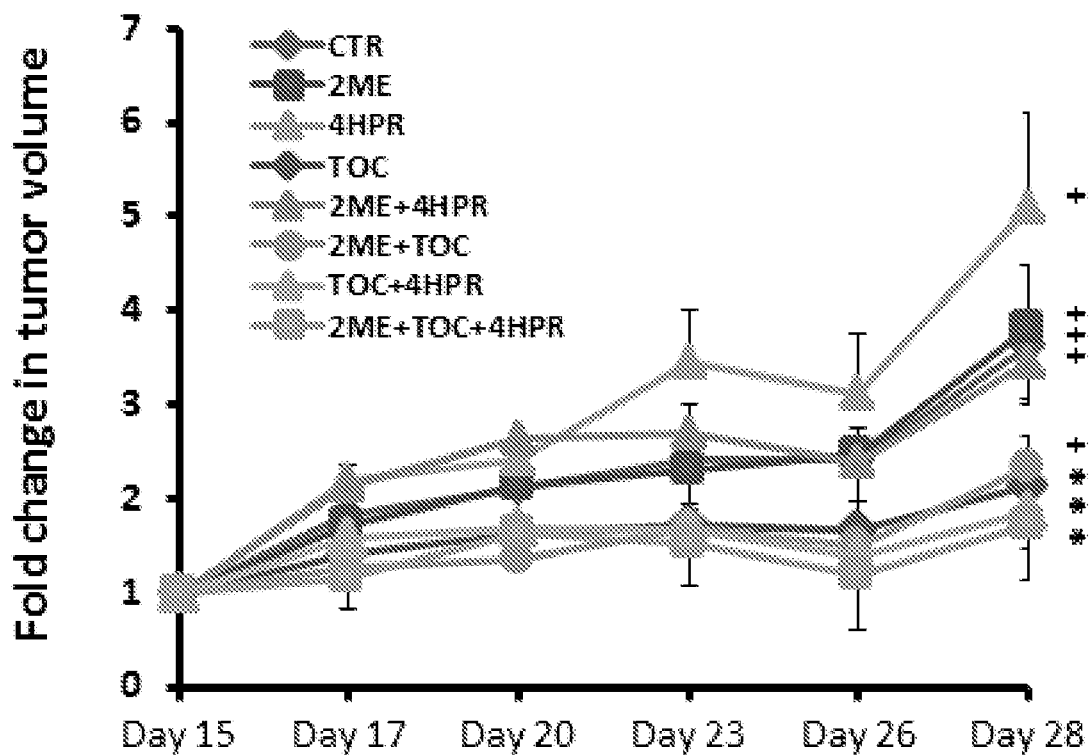
FIG. 6A shows the fold change in tumor volume in mice over time with single or combination treatment of fenretinide (4-HPR), 2-methoxyestradiol (2-ME), and tocilizumab (TOC). One million SCC2095sc cells (suspended in 100 μl Matrigel) were subcutaneously injected in in flanks of 6 to 7 week old male nude mice (n=6 per treatment group). By day 14 post injection, all mice had palpable and measurable tumors. Treatment began on day 15. Caliper-based tumor measurements were recorded daily and final tumor volumes calculated via tumor volume V=(length×width)×½. Treatment groups consisted of: 1) control (PBS injections)+blank (no drug) polylactide co-glycolide (PLGA) implants, 2) 2-methoxyestradiol (2-ME) (1 μg/100 μl PBS, b.i.d.)+blank PLGA implant, 3) fenretinide (4-HPR) releasing PLGA implant+PBS injections, 4) tocilizumab (TOC) q.d. (0.3 μg/100 μl PBS)+PLGA blank implant, 5) 2-ME (1 μg/100 μl PBS, b.i.d.)+4-HPR releasing PLGA implant, 6) 2-ME (1 μg/100 μl PBS, b.i.d.)+TOC q.d. (0.3 μg/100 μl PBS)+blank PLGA implant, 7) TOC q.d. (0.3 μg/100 μl PBS)+4-HPR releasing PLGA implant, 8) 2-ME (1 μg/100 μl PBS, b.i.d.)+TOC q.d. (0.3 μg/100 μl PBS)+4-HPR releasing PLGA implant. In previous studies that employed younger mice tumors of varying sizes were disbursed among all treatment groups. Due to the older age of mice >6 weeks and the accompanying cage aggression tumor size distribution was not feasible in these studies. As a result, mean tumor volumes varied appreciably among treatment groups. PLGA implants (trocar placement) and injections were placed in the center of the tumor. Fluid dispersion throughout tumor was noted during injections. At day 28 post OSCC xenograft placement the mice were sacrificed, OSCC tumors along with lung and liver tissues and sera were harvested (for PK and histologic analyses). These data show three groups i.e. TOC, TOC+4-HPR, and triple treatment (TOC+2-ME+4-HPR) were the only treatments that prevented a significant increase in tumor volume (paired t test). Provided the discrepancy in pretreatment tumor volumes (TOC the lowest, triple treatment second highest with its mean nearly two fold higher than TOC mean), the TOC+2-ME+4-HPR data are especially creditable.
Figure 6B:
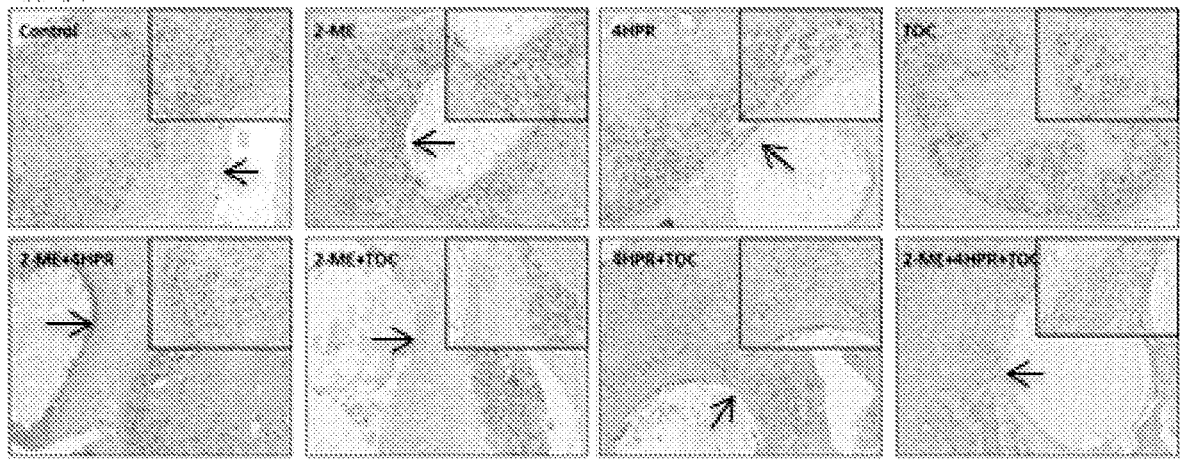
FIG. 6B shows Ki-67 and cleaved caspase 3 immunohistochemical stains to assess qualitative treatment effects on tumor cells' proliferation and apoptosis. IHC images representative of all of the groups are presented. The PLGA implants are visible as a clear cylindrical object in every photomicrograph except the TOC and 2-ME+TOC treatment. To facilitate PLGA implant recognition, arrows have been placed within the implants. Both the Ki-67 and caspase 3 stains are located within the nucleus. Qualitative Ki67 staining assessment was most apparent at the periphery of the tumors in all groups. In contrast to the abundant Ki-67 staining, cleaved caspase 3 was not nearly as prominent.
Figure 6B:
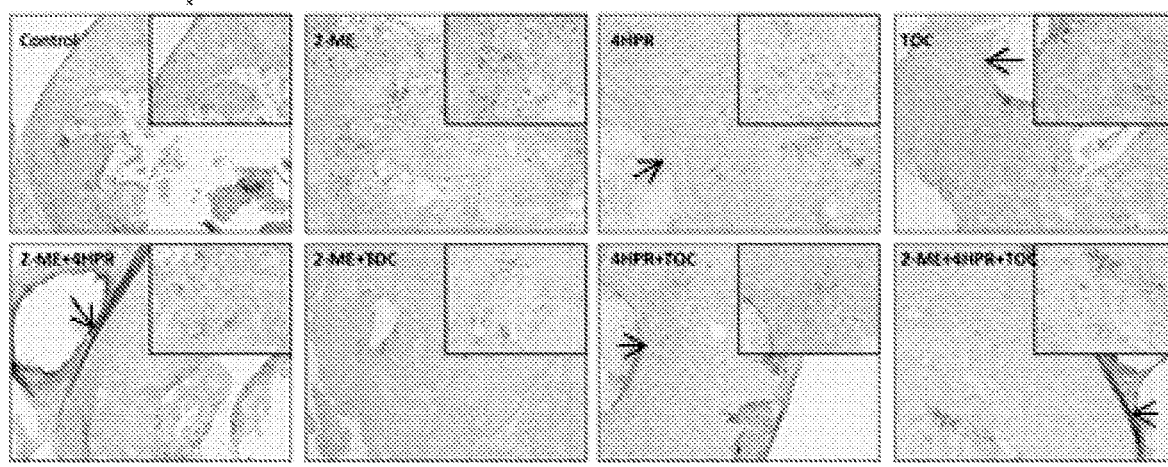
Figure 6C:
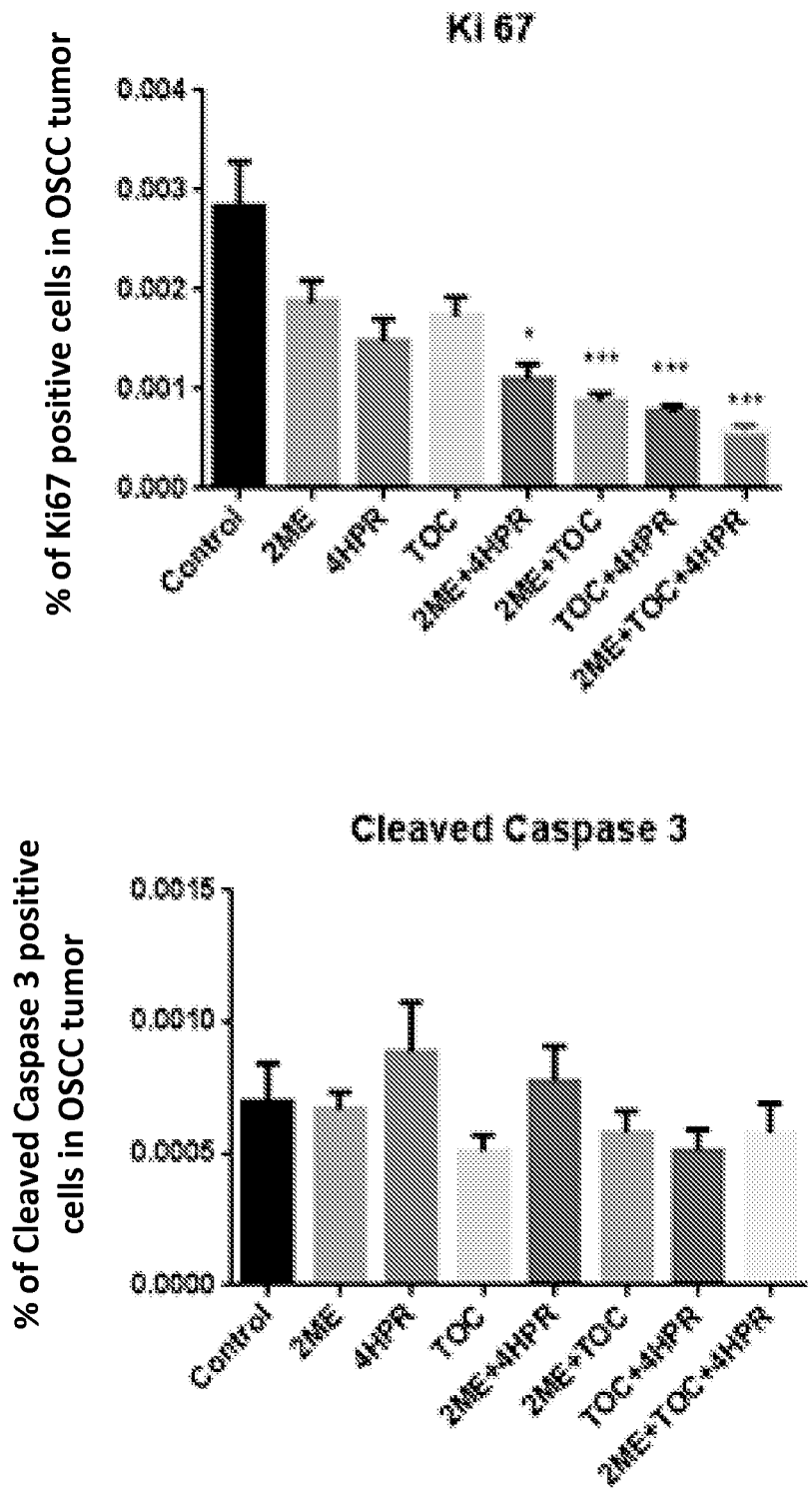
FIG. 6C shows bar graphs quantifying the Ki-67 and cleaved caspase 3 immunohistochemical stains. The image analysis revealed that all treatments suppressed tumor cell proliferation relative to the untreated tumor. Furthermore, significant inhibition of proliferation (as assessed by % of tumor cells demonstrating Ki-67 labeling) was seen in these groups: 2-ME+4-HPR+TOC, TOC+4-HPR, 2-ME+TOC (all $p<0.001$) and 2-ME+4-HPR ($p<0.05$) Kruskal Wallis with Dunns' Multiple Comparison post hoc test. Although cleaved caspase 3 nuclear staining was present, none of the treatments showed any significant effects relative to the matched control tumors. Image analysis did not reveal any inter-group differences with regard to caspase 3 labeling. (Image scale 4× and 10× for smaller and larger photomicrographs, respectively).

IHC studies provided further insights into treatment-tumor effects. Ki-67 labeling was most apparent at tumor peripheries; findings consistent with relatively hypoxic tumor cores. Quantitative Ki-67 analyses revealed that any treatment reduced tumor cell proliferation while significant reduction in tumor cell labeling was present in the triple treatment, TOC+4-HPR, 2-ME+TOC and 2ME+4-HPR groups (see FIGS. 6B and 6C). As the tumors in the 4-HPR group were so large, part of the Ki-67 decrease may reflect necrotic tumor foci due to inadequate angiogenesis to support the tumor mass. Although two established apoptosis-inducing drugs (2-ME and 4-HPR) were employed, low levels of cleaved caspase 3 were detected in all groups (FIGS. 6 and 6C). These data may reflect both a relatively short half-life (~8 hours for activated caspase 3 [49]) and additional forms of cancer cell death including necrosis, senescence and autophagy [50]. Treatment effects on differentiation were evaluated by involucrin staining. While all experimental groups contained involucrin, qualitatively the most intense expression was observed in the 2-ME and 4-HPR+TOC groups. Despite the challenges of daily injections of drugs with short or intermediate half-lives (2-ME~4 h, TOC~0.8 days), pH dependent binding (acidic pH decreases TOC binding), and limited diffusion capacity (4-HPR), the data show efficacy of the selected chemopreventives to suppress growth in established OSCC tumors. These data show the chemopreventives' ability to abort microtumor foci. Finally, the absence of deleterious effects to the overlying epidermis emphasizes the chemopreventives' safety during local delivery.

Risk reduction and primary chemoprevention clearly remain the optimal OSCC management approach. Provided the often fatal consequences of recurrent OSCCs and lack of effective intervention options to prevent tumor recurrence, development of a well-tolerated and effective secondary chemoprevention strategy is warranted. The benefits from optimized controlled-release local delivery implants that stabilize drugs, remove peak and valley drug levels, eliminate issues with systemic toxicities and patient compliance and facilitate drug diffusion throughout the previous surgical site to eradicate OSCC recurrence are shown in this example.

REFERENCES CITED IN THIS EXAMPLE

All cited references are herein incorporated by reference for all purposes.
1. Huber M A, Tantiwongkosi B. Oral and Oropharyngeal Cancer. Med Clin N Am 2014; 98:1299-1321.
2. Gleber-Netto F O, Braakhuis B J, Triantafyllou A, Takes R P, Kelner N, Rodrigo J P, et al. Molecular events in relapsed oral squamous cell carcinoma: Recurrence vs secondary primary tumor. Oral Oncol 2015; 51:738-44.
3. Brockstein B E. Management of Recurrent Head and Neck Cancer. Recent Progress and Future Directions. Drugs 2011; 71:1551-9.
4. Arora A, Scholar E M. Role of Tyrosine Kinase Inhibitors in Cancer Therapy. J Pharm Exp Therapeutics 2005; 315:971-9.
5. Dziadziuszko R, Jassem J. Epidermal growth factor receptor (EGFR) inhibitors and derived treatments. Ann Oncology 2012; 23:193-6.
6. Molife L R, Omlin A, Jones R J, Karavasilis V, Bloomfield D, Lumsden G, et al. Randomized Phase II trial of nintedanib, afatinib and sequential combination in castration-resistant prostate cancer. Future Oncol 2014; 10:219-31.
7. Stanam A, Love-Homan L, Joseph T S, Espinosa-Cotton M, Simons A L. Upregulated interleukin-6 expression contributes to erlotinib resistance in head and neck squamous cell carcinoma. Mol Oncol 2015; 9:1371-83.
8. Specenier P, Vermorken J B. Cetuximab: its unique place in head and neck cancer treatment. Biologics 2013; 7:77-90.

9. Sun C, Bernards R. Feedback and redundancy in receptor tyrosine kinase signaling: relevance to cancer therapies. Trends Biochem Sci 2014; 39:465-74.
10. Bahleda R, Hollebecque A, Varga A, Gazzah A, Massard C, Deutsch E, et al. Phase I study of afatinib combined with nintedanib in patients with advanced solid tumours. Br J Cancer 2015; 113:1413-20.
11. Furtek S L, Backos D S, Matheson C J, Reigan P. Strategies and approaches of targeting STAT3 for cancer treatment. ACS Chem Biol 2016; 11:308-18.
12. Yu H, Lee H, Herrmann A, Buettner R, Jove R. Revisiting STAT3 signaling in cancer: new and unexpected biological functions. Nat Rev Cancer 2014; 14:736-46.
13. Yu H, Pardoll D, Jove R. STATs in cancer inflammation and immunity: a leading role for STAT3. Nat Rev Cancer 2009; 9:798-809.
14. Lee H, Zhang P, Herrmann A, Yang C, Xin H, Wang Z, et al. Acetylated STAT3 is crucial for methylation of tumor-suppressor gene promoters and inhibition by resveratrol results in demethylation. Proc Natl Acad Sci USA 2012; 109: 7765-69.
15. Jinno T, Kawano S, Maruse Y, Matsubara R, Goto Y, Sakamoto T, Hashiguchi Y, et al. Increased expression of interleukin-6 predicts poor response to chemoradiotherapy and unfavorable prognosis in oral squamous cell carcinoma. Oncol Rep 2015; 33:2161-68.
16. Chang P Y, Kuo Y B, Wu T L, Liao C T, Sun Y C, Yen T C, et al. Association and prognostic value of serum inflammation markers in patients with leukoplakia and oral cavity cancer. Clin Chem Lab Med 2013; 51:1291-1300.
17. Ogura M, Uchida T, Terui Y, Hayakawa F, Kobayashi Y, Taniwaki M, et al. Phase I study of OPB-51602, an oral inhibitor of signal transducer and activator of transcription 3, in patients with relapsed/refractory hematological malignancies. Cancer Sci 2015; 106:896-901.
18. Wong A L, Soo R A, Tan D S, Lee S C, Lim J S, Marban P C, et al. Phase I and biomarker study of OPB-51602, a novel signal transducer and activator of transcription (STAT) 3 inhibitor, in patients with refractory solid malignancies. Ann Oncol 2015; 26:998-1005.
19. Logue J S, Morrison D K. Complexity in the signaling network: insights from the use of targeted inhibitors in cancer therapy. Genes Dev 2012; 26:641-50.
20. Naithani R, Huma L C, Moriarty R M, McCormick D L, Mehta R G. Comprehensive review of cancer chemopreventive agents evaluated in experimental carcinogenesis models and clinical trials. Curr Med Chem 2008; 15:1044-71.
21. Han B B, Li S, Tong M, Holpuch A S, Spinney R, Wang D, et al. Fenretinide perturbs focal adhesion kinase in premalignant and malignant human Oral Keratinocytes. Fenretinide's chemopreventive mechanisms include ECM interactions. Cancer Prev Res 2015; 8:419-30.
22. Jones S A, Scheller J, Rose-John S. Therapeutic strategies for the clinical blockade of IL-6/gp130 signaling. J Clin Invest 2011; 121:3375-83.
23. Mooberry S L. Mechanism of action of 2-methoxyestradiol: new developments. Drug Resist Updat 2003; 6:355-61.
24. Takahashi N, Sausville E A, and Breitman T R. N-(4-Hydroxyphenyl)retinamide (Fenretinide) in combination with retinoic acid enhances differentiation and retinoylation of proteins. Clin Cancer Res 1995; 1:637-42.
25. Mueck A O, Seeger H. 2-Methoxyestradiol-Biology and mechanism of action. Steroids 2010; 75:625-31.
26. Poindessous V, Ouaret D, El Ouadrani K, Battistella A, Megalophonos V F, Kamsu-Kom N, Petitprez A, Escargueil A E, Boudou P, Dumont S et al. EGFR- and VEGF(R)-targeted small molecules show synergistic activity in colorectal cancer models refractory to combinations of monoclonal antibodies. Clin Cancer Res 2011; 17:6522-30.
27. Trott O, Olson A J. AutoDock Vina: Improving the speed and accuracy of docking with a new scoring function, efficient optimization, and multithreading. J Comput Chem 2010; 31:455-61.
28. Berman H, Henrick K, Nakamura H. Announcing the worldwide Protein Data Bank. Nat Struct Biol 2003; 10:980.
29. Yu W, Xiao H, Lin J, Li C. Discovery of novel STAT3 small molecule inhibitors via in silico site-directed fragment-based drug design. J Med Chem 2013; 56:4402-12.
31. Hantschel O, Superti-Furga G. Regulation of the C-Abl and Bcr-Abl tyrosine kinases. Nat Rev 2004; 5:33-44.
32. Suh Y, Jo S Y, Lee H Y, Lee C. Inhibition of IL-6/STAT3 axis and targeting Axl and Tyro3 receptor tyrosine kinases by apigenin circumvent taxol resistance in ovarian cancer cells. Int J Oncol 2015; 46:1405-11.
33. Jemma A B, Sallami S, Ramarli D, Colombatti M, Oueslati R. The proinflammatory cytokine, IL-6, and its interference with bFGF signaling and PSMA in prostate cancer cells. Inflammation 2013; 36:643-50.
34. Harada K, Ferdous T, Itashiki Y, Takii M, Mano T, Mori Y, et al. Cepharanthine inhibits angiogenesis and tumorigenicity of human oral squamous cell carcinoma cells by suppressing expression of vascular endothelial growth factor and interleukin-8. Int J Oncol 2009; 35:1025-35.
35. Garcia R, Bowman T L, Niu G, Yu H, Minton S, Muro-Cacho C A, et al. Constitutive activation of Stat3 by the Src and JAK tyrosine kinases participates in growth regulation of human breast carcinoma cells. Oncogene 2001; 20:2499-513.
36. Lin J, Arlinghaus R. Activated c-Abl tyrosine kinase in malignant solid tumors. Oncogene 2008; 27:4385-91.
37. Fury M G, Baxi S, Shen R, Kelly K W, Lipson B L, Carlson D, et al. Phase II study of saracatinib (AZD0530) for patients with recurrent or metastatic head and neck squamous cell carcinoma (HNSCC). Anticancer Res 2011; 31:249-53.
38. Brooks H D, Glisson B S, Bekele B N, Johnson F M, Ginsberg L E, El-Naggar A, et al. Phase 2 study of dasatinib in the treatment of head and neck squamous cell carcinoma. Cancer 2011; 117:2112-9.
39. Campos-Sandoval J A, Redondo C, Kinsella G K, Pal A, Jones G, Eyre G S, et al. Fenretinide derivatives act as disrupters of interactions of serum retinol binding protein (sRBP) with transthyretin and the sRBP receptor. J Med Chem 2011; 54:4378-87.
40. Lee T L, Yeh J, Van Waes C, Chen Z. Epigenetic modification of SOCS-1 differentially regulates STAT3 activation in response to interleukin-6 receptor and epidermal growth factor receptor signaling through JAK and/or MEK in head and neck squamous cell carcinomas. Mol Cancer Ther 2006; 5:8-19.
41. Yang J, Liao X, Agarwal M K, Barnes L, Auron P E, Stark G R. Unphosphorylated STAT3 accumulates in response to IL-6 and activates transcription by binding to NFkappaB. Genes Dev 2007; 21:1396-1408.
42. Yu Y, Wan Y, Huang C. The biological functions of NF-κB1 (p50) and its potential as an anti-cancer target. Curr Cancer Drug Targets 2009; 9:566-71.

43. Kumar A P, Garcia G E, Orsborn J, Levin V A, Slaga T J. 2-Methoxyestradiol interferes with NFκB transcriptional activity in primitive neuroectodermal brain tumors: implications for management. Carcinogenesis 2003; 24:209-16.
44. Chalaris A, Garbers C, Rabe B, Rose-John S, Scheller J. The soluble Interleukin 6 receptor: Generation and role in inflammation and cancer. Eur J Cell Biol 2011; 90:484-94.
45. Fofaria M N, Srivastava S K. STAT3 induces anoikis resistance, promotes cell invasion and metastatic potential in pancreatic cancer cells. Carcinogenesis 2015; 36:142-50.
46. Ward K K, Tancioni I, Lawson C, Miller N L, Jean C, Chen X L, et al. Inhibition of focal adhesion kinase (FAK) activity prevents anchorage-independent ovarian carcinoma cell growth and tumor progression. Clin Exp Metastasis 2013; 30:579-94.
47. Lee C H, Yu C C, Wang B Y, Chang W W. Tumorsphere as an effective in vitro platform for screening anticancer stem cell drugs. Oncotarget 2016; 7:1215-26.
47. Ricker J L, Chen Z, Yang X P, Pribluda V S, Swartz G M, Van Waes C. 2-Methoxyestradiol inhibits Hypoxia-Inducible Factor 1α, tumor growth, and angiogenesis and augments Paclitaxel efficacy in Head and Neck Squamous Cell Carcinoma. Clin Cancer Res 2004; 10:8665-73.
48. Shinriki S, Jono H, Ota K, Ueda M, Kudo M, Ota T, et al. Humanized anti-Interleukin-6 Receptor antibody suppresses tumor angiogenesis and in vivo growth of human Oral Squamous Cell Carcinoma. Clin Cancer Res 2009; 15:5426-34.
49. Walsh J C, Logue S E, Luthi A U, Martin S J. Caspase-1 promiscuity is counterbalanced by rapid inactivation of processed enzyme. J Biol Chem 2011; 286:32513-24.
50. Brown J M, Attardi L D. The role of apoptosis in cancer development and treatment response. Nat Rev Cancer 2005; 5:231-7.

Figure 7:
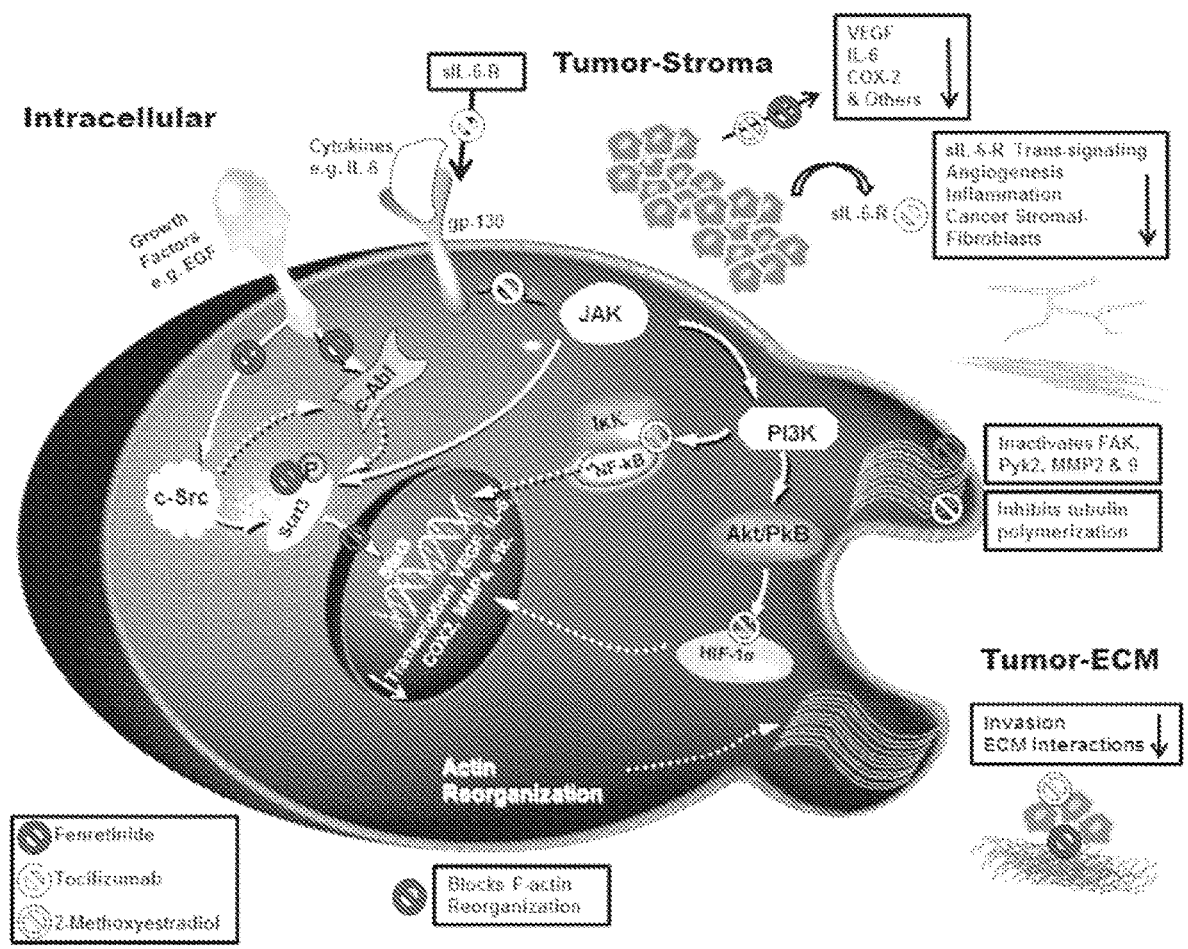
FIG. 7 shows a schematic of a cell depicting the action of the therapeutic agents fenretinide, 2-methoxyestradiol, and tocilizumab.

Example 2. Chemoprevention Using Fenretinide, 2-Methoxyestradiol, and Tocilizumab As shown in FIG. 7, the therapeutic effect of fenretinide, 2-methoxyestradiol, and tocilizumab is multifaceted. 4-HPR: 1) binds with high affinity and obstructs the ATP binding sites of FAK and Pyk2 (kinases essential for tumor-ECM interactions), 2) perturbs F-actin organization, and 3) significantly inhibits OSCC migration and invasion.

Figure 8A:
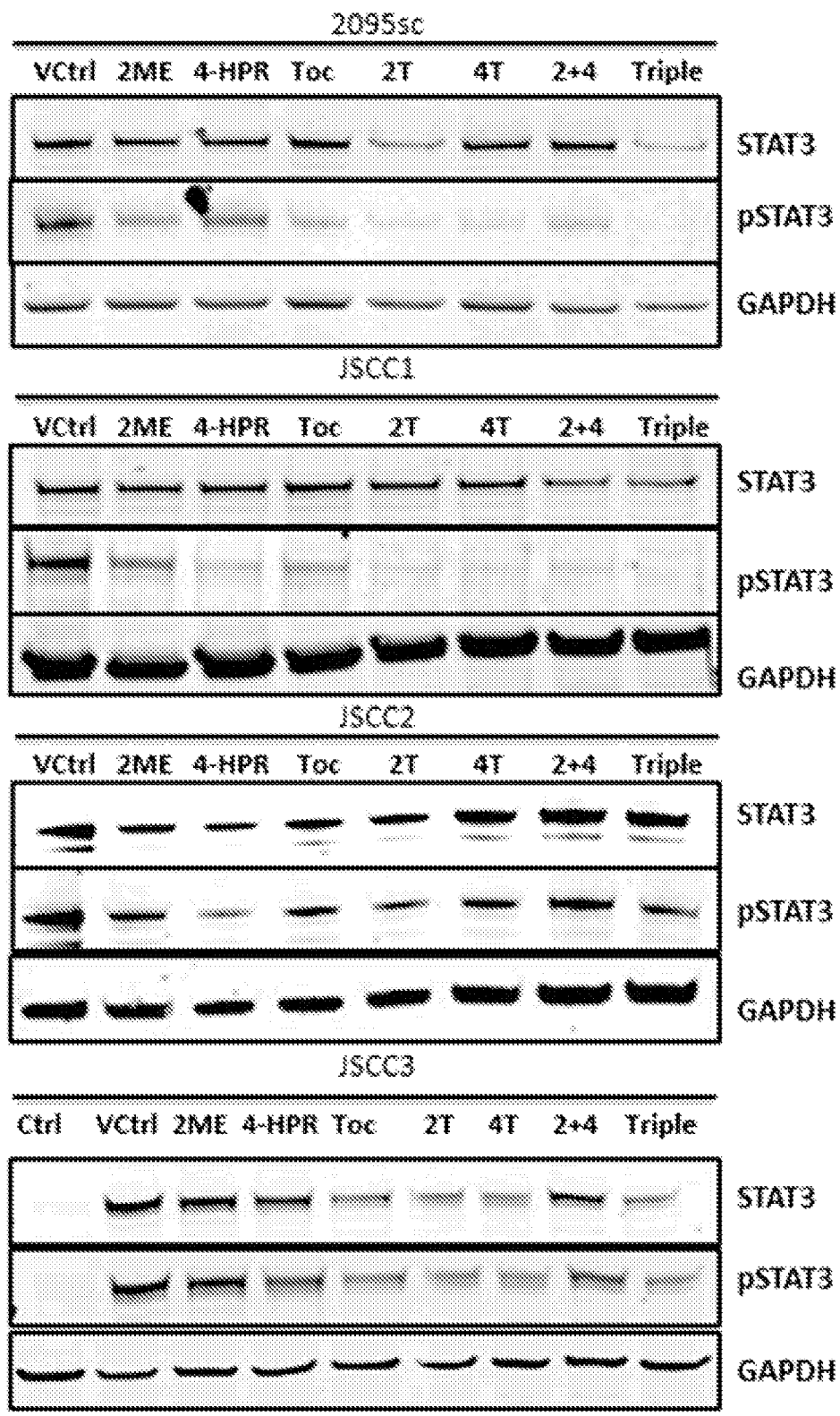
FIGS. 8A and 8B show STAT3 phosphorylation levels after treatment with single, double, or triple combinations of the therapeutic agents fenretinide, 2-methoxyestradiol, and tocilizumab. (A) A Western blot of protein levels for STAT3, pSTAT3, and GAPDH in cell lines (2095sc, JSCC1, JSCC2, JSCC3) treated for 24 hours with control (0.1% DMSO) (VCtrl), 2.5 μM 2-ME, 5 μM 4-HPR, 1 μg/ml TOC, 2.5 μM 2-ME and 1 μg/ml TOC (2T), 5 μM 4-HPR and 2.5 μM 2-ME (4T), 5 μM 4-HPR and 2.5 μM 2-ME (2+4), or 5 μM 4-HPR, 2.5 μM 2-ME, and 1 μg/ml TOC (Triple) (initial agent concentrations same for single and combinations). (B) Bar graph of pSTAT3 protein levels (ratio to Control) in cell lines (2095sc, JSCC1, JSCC2, JSCC3) treated for 24 hours with control (0.1% DMSO) (VCtrl), 2.5 μM 2-ME, 5 μM 4-HPR, 1 μg/ml TOC, 2.5 μM 2-ME and 1 μg/ml TOC (2T), 5 μM 4-HPR and 2.5 μM 2-ME (4T), 5 μM 4-HPR and 2.5 μM 2-ME (2+4), or 5 μM 4-HPR, 2.5 μM 2-ME, and 1 μg/ml TOC (Triple) (initial agent concentrations same for single and combinations).
Figure 8B:
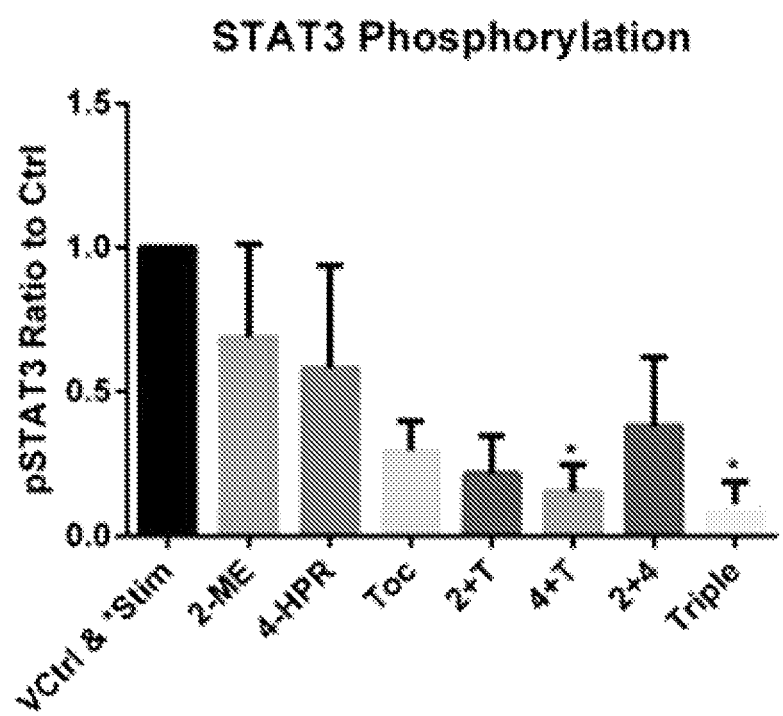

Example 3. Single and Combination Chemoprevention Treatment on Total STAT3 Phosphorylation The effect of single and combination treatment on total STAT3 phosphorylation is shown in FIG. 8. All cell lines with constitutive pSTAT3 expression (2095sc, JSCC1, JSCC2) were sera deprived for 24 h, followed by an additional 24 hour of treatment in sera-free medium that contained: control (0.1% DMSO), 5 µM 4-HPR, 2.5 µM 2-ME, 1 µg/ml TOC (initial agent concentrations same for single and combinations). As the JSCC3 cells don't constitutively express pSTAT3, these cells underwent 24 h stimulation in base medium supplemented with 10 ng/mL of IL-6 and 5 ng/mL of TGF-α, followed by harvest. Treatment responsiveness once again highlights inter cell line heterogeneity. 2095sc cells, and to a lesser extent JSCC21 and JSCC3 cells demonstrated reduction of both STAT3 and pSTAT3 proteins post treatment. While triple treatment demonstrated less of a STAT3 reduction in JSCC2 cells, it did diminish pSTAT3, albeit to a lesser extent than the other constitutively active cell lines. Despite cell line variations, the treatment combinations of TOC+4-HPR and TOC+4-HPR+2-ME induced significant inhibition of STAT3 phosphorylation (p<0.05, n=4, Kruskal Wallis with Dunn's Multiple Comparison post hoc test). These inter cell line variations are likely multifactorial and reflect a combination of effects including intracellular drug levels, metabolism and drug egress and target protein stabilization and/or ubiquitination.

Example 4. Markers of OSCC Cancers

Figure 9A:
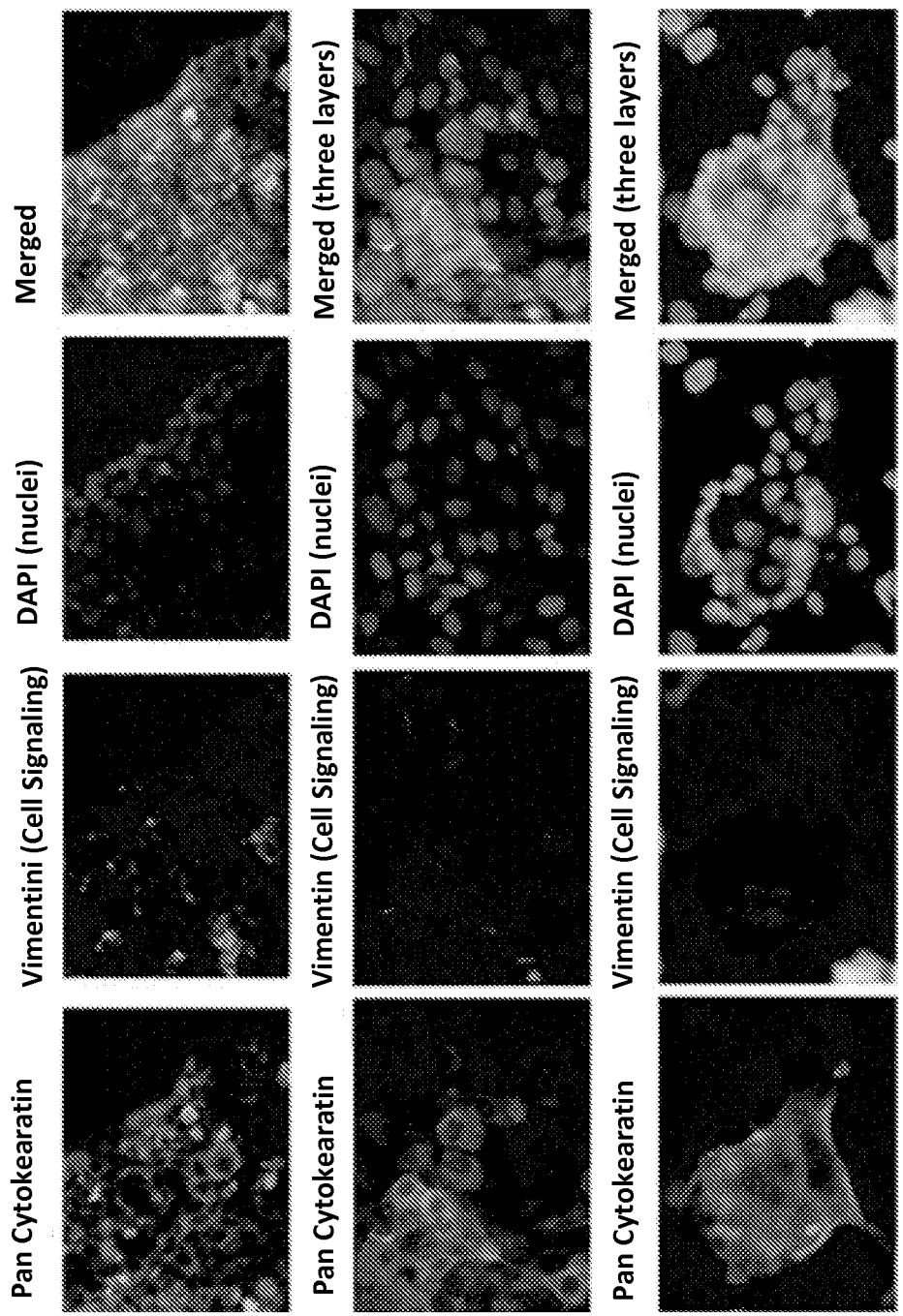
FIG. 9A shows a panel of immunofluorescent staining from OSCC tumors showing staining for cytokeratin, vimentin, DAPI, or a merged image. The top row of images show staining from the cell line JSCC1. The middle row of images show staining from the cell line JSCC2. The bottom row of images show staining from the cell line JSCC3.

The clinical stage of parent OSCC tumors is shown in FIG. 9A. Immunofluorescent staining revealed tumor derived cell lines all demonstrate the presence of cytokeratin with variable co-expression of the "mesenchymal" marker vimentin. Coexpression of cytokeratin and vimentin is consistent with an epithelial to mesenchymal transition.

Figure 9B:
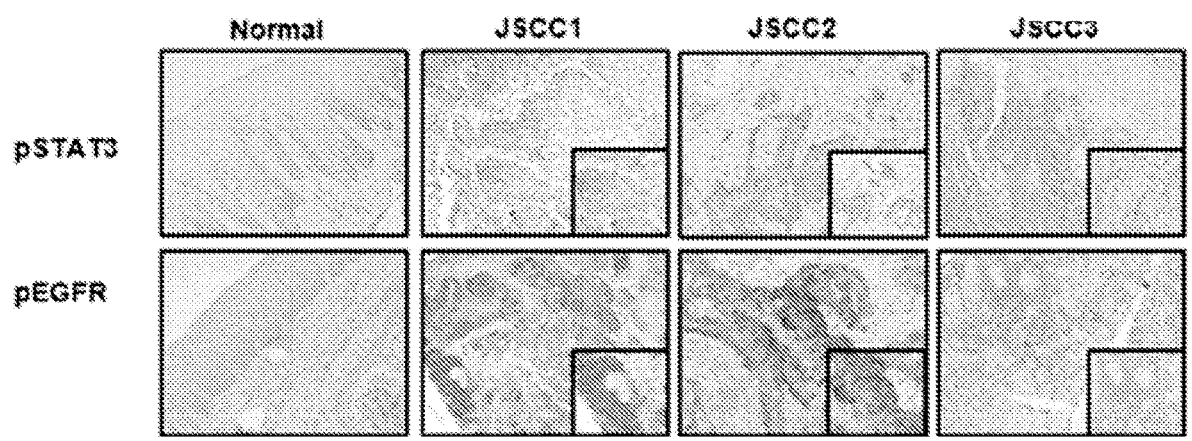
FIG. 9B shows a panel of immunofluorescent staining from OSCC tumors showing staining for pSTAT3 or pEGFR. (100× image scale larger photo, 200× image scale inset).

As seen in FIG. 9B, clinically and histologically normal oral mucosa demonstrates modest pSTAT3 nuclear staining that is restricted to basal layer keratinocytes and shows no apparent pEGFR expression. In contrast, OSCC tumor tissues demonstrate more profound pSTAT3 expression, often at the peripheral aspects of the tumor islands. JSCC1 and JSCC2 tumor tissues exhibit robust membranous and cytosolic pEGFR staining, JSCC3 levels are modest.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

We claim:

1. A controlled-release pharmaceutical implant for localized delivery of tocilizumab, fenretinide, and 2-methoxyestradiol, wherein the implant comprises first, second, and third contiguous poly(lactic-co-glycolic acid) (PLGA) segments configured in a millicylinder geometry, wherein each PLGA polymer segment comprises a single therapeutic agent, wherein the first segment comprises tocilizumab in end-capped 50/50 PLGA polymer having an average molecular weight of about 60 kDa, the second segment comprises either fenretinide in acid-capped PLGA polymer having an average molecular weight of about 13-24 kDa or fenretinide in 60% 50:50 acid end-capped PLGA polymer having an average molecular weight of about 24-38 kDa, and the third segment comprises 2-methoxyestradiol in acid-capped 50/50 PLGA polymer having an average molecular weight of about 13-24 kDa.

2. The controlled-release pharmaceutical implant of claim 1, wherein the implant provides an initial burst release of less than 20% of tocilizumab and 2-methoxyestradiol in the first day after administration.

3. The controlled-release pharmaceutical implant of claim 1, wherein the second PLGA polymer segment comprising fenretinide comprises 60% 50:50 acid end-capped PLGA having an average molecular weight of 24-38 kDa.

* * * * *